(12) United States Patent
Klessig et al.

(10) Patent No.: US 6,495,737 B1
(45) Date of Patent: Dec. 17, 2002

(54) METHODS AND COMPOSITIONS FOR IMPROVING SALICYLIC ACID-INDEPENDENT SYSTEMIC ACQUIRED DISEASE RESISTANCE IN PLANTS

(75) Inventors: Daniel F. Klessig, Bridgewater; Ailan Guo, Piscataway, both of NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 08/909,125

(22) Filed: Aug. 11, 1997

Related U.S. Application Data

(60) Provisional application No. 60/024,033, filed on Aug. 12, 1996.

(51) Int. Cl.$^7$ .................. C12N 15/82; C12N 15/84; C12N 5/04; A01H 4/00
(52) U.S. Cl. ............ 800/279; 536/23.6; 536/24.1; 435/69.1; 800/278
(58) Field of Search .................. 536/23.6, 24.1; 435/69.1; 800/205

(56) References Cited

PUBLICATIONS

J.K. Beetham, et al., Archives of Biochemistry and Biophysics, 305: 197–201 (1993).
M. Knehr, et al., The Journal of Biological Chemistry, 268: 17623–17627 (1993).
I.A.M.A Penninckx, et al., The Plant Cell, 8: 2309–2323 (1996).
C.M.J. Pieterse, et al., The Plant Cell, 8: 1225–1237 (1996).
J. Shah, et al, MPMI, 10:, 69–78 (1997).
A. Stapleton, et al., The Plant Journal, 6: 251–258 (1994).
J. Glazebrook, et al., Genetics, 143: 973–982 (1996).
D.F. Grant, et al., The Journal of Biological Chemistry, 268: 176828–17633 (1993).
K. Herbers, et al., The Plant Cell, 8: 793–803 (1996).
T. Kiyosue, et al., The Plant Journal, 6: 259–260 (1994).
S. Vidal, et al., The Plant Journal, 11: 115–123 (1997).
Penincky et al. The Plant Cell. 1996. Dec. issue. vol. 8: 2309–2323, 1996.*
Henning et al. Plant Journal. Sep. issue. vol. 4: 481–493, 1993.*
Vernooij et al. Plant Molecular Biology. 1995. Dec. issue. vol. 29: 959–968, 1995.*

* cited by examiner

*Primary Examiner*—Gary Benzion
*Assistant Examiner*—Ousama M- Faiz Zaghmout
(74) *Attorney, Agent, or Firm*—Dann, Dorfman, Herrell and Skillman

(57) ABSTRACT

The present invention provides methods and materials that enhance a plant's resistance to certain pathogens. A novel pathway is described and has been designated with the acronym, SI-SAR pathway, for salicylic acid-independent systemic acquired resistance. DNA constructs and methodologies are provided that facilitate the identification of compounds that activate this pathway. Methods are provided to enable the identification of novel genes and signaling components that are expressed when the SI-SAR pathway is activated. Transgenic plants with altered expression of these novel genes or signaling components of the pathway are expected to have enhanced resistance to plant pathogens. Also provided is a novel, pathogen-induced epoxide hydrolase that is inducible in the absence of SA.

2 Claims, 12 Drawing Sheets

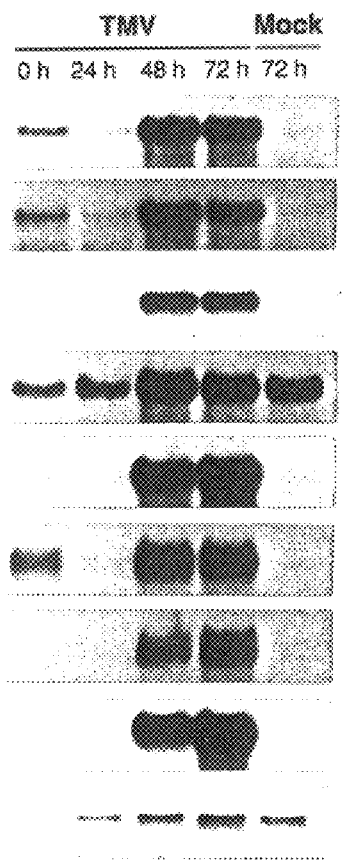
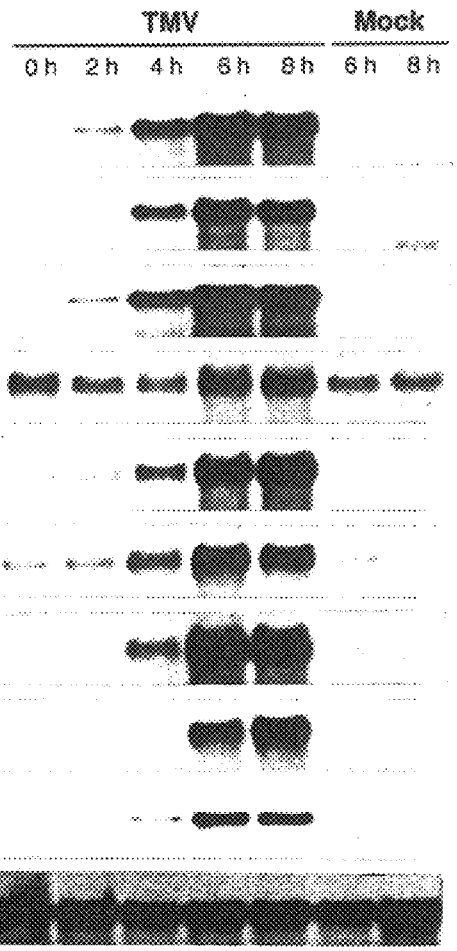
Figure 1

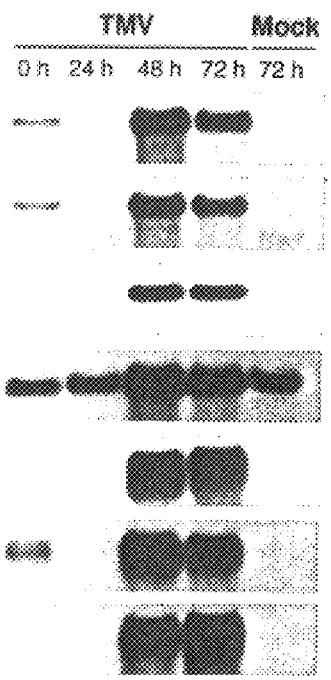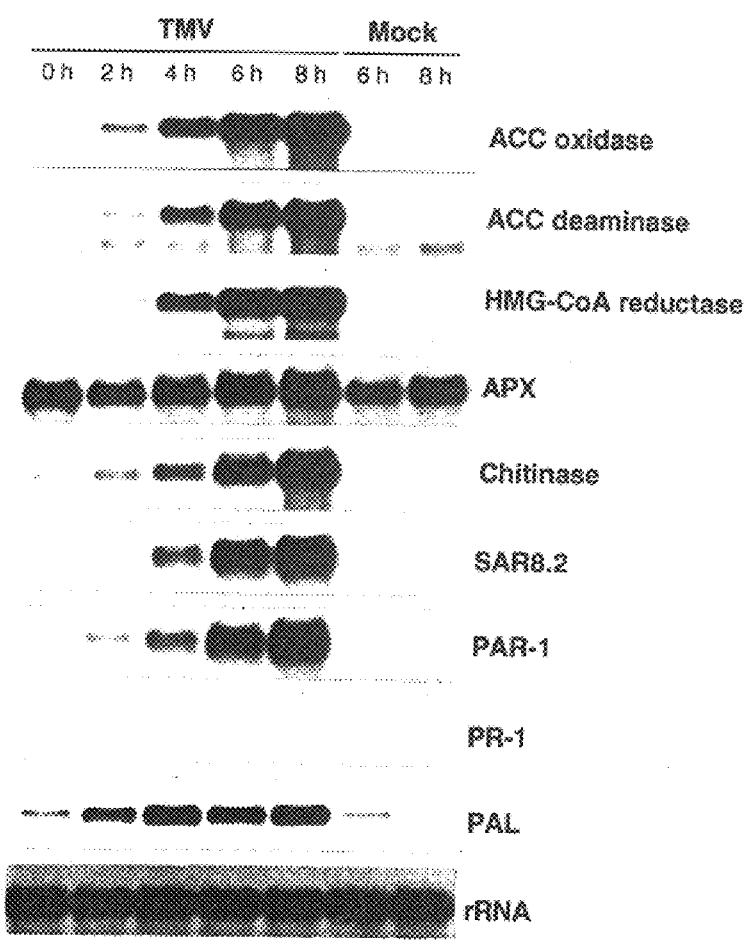
Figure 3

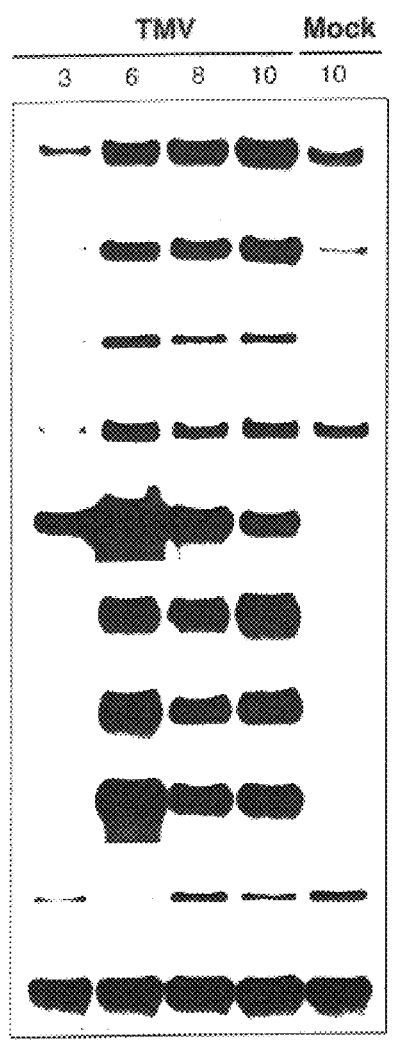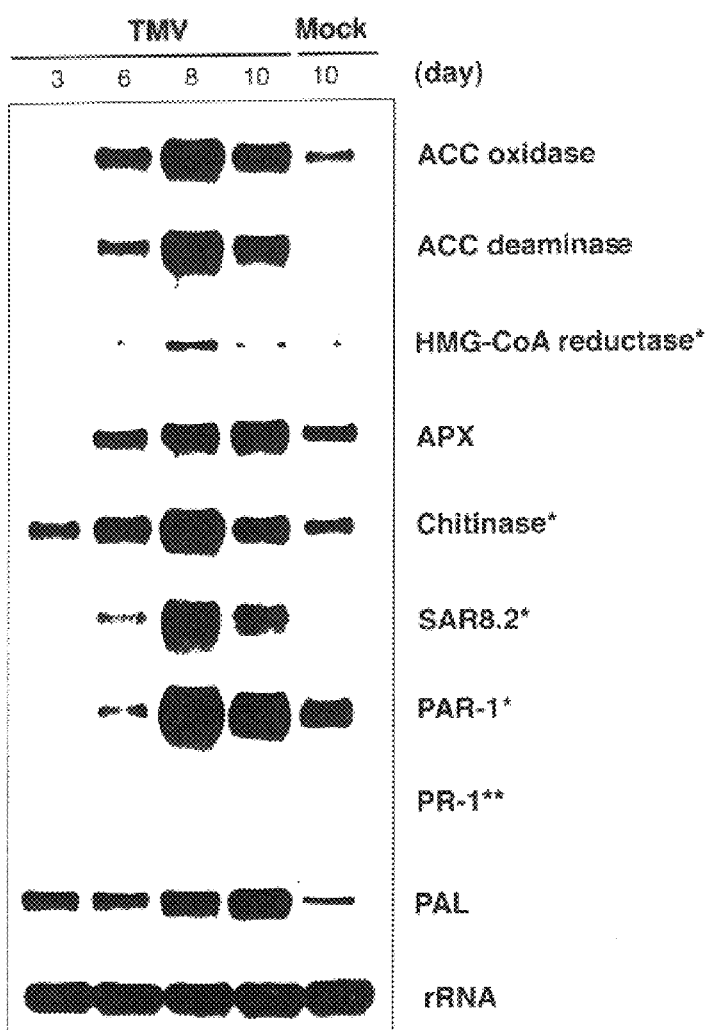
Figure 5

Fig. 6A

```
AACACATTGACTTGTCATTAATTCTCTTTAATTTTTGTTGCACTCCCATCAAACCTTCCT    60
ACCTTACGAAAATGGAGAAGATTCAGCACAATTATGTGGATGTAAGAGGACTCAAGCTTC   120
            M  E  K  I  Q  H  N  Y  V  D  V  R  G  L  K  L  H
ACATTGCAGAGATTGGAACAGGCCCTGCAGTATTCTTTCTTCATGGATTCCCTGAGATAT   180
 I  A  E  I  G  T  G  P  A  V  F  F  L  H  G  F  P  E  I  W
GGTACTCGTGGAGGCATCAGATGATAGCAGTAGCGGATGCAGGATTTCGAGGCATAGCCC   240
 Y  S  W  R  H  Q  M  I  A  V  A  D  A  G  F  R  G  I  A  P
CTGACTTCAGAGGCTATGGTTTGTCTGAATTGCCTGCAGAACCGGAGAAGACGACATTCA   300
 D  F  R  G  Y  G  L  S  E  L  P  A  E  P  E  K  T  T  F  R
GGGACCTTGTCGATGATCTTCTGGACATGCTTGATTCATTAGGCATCCACCAGGTTTTTC   360
 D  L  V  D  D  L  L  D  M  L  D  S  L  G  I  H  Q  V  F  L
TTGTGGGGAAGGATTTTGGAGCTCGAGTAGCTTACCATTTTGCACTCGTACACCCTGATA   420
 V  G  K  D  F  G  A  R  V  A  Y  H  F  A  L  V  H  P  D  R
GAGTTTCAACTGTTGTAACATTAGGTGTGCCCTTTCTTCTCACTGGTCCAGAAACATTTC   480
 V  S  T  V  V  T  L  G  V  P  F  L  L  T  G  P  E  T  F  P
CTCGAGATCTCATTCCCAATGGGTTCTATATGTTGAGATGGCAGGAACCAGGGCGAGCTG   540
 R  D  L  I  P  N  G  F  Y  M  L  R  W  Q  E  P  G  R  A  E
AAAAGGACTTTGGGCGTTTTGATACAAAAACAGTAGTTAAGAACATATATACTATGTTCT   600
 K  D  F  G  R  F  D  T  K  T  V  V  K  N  I  Y  T  M  F  S
CTGGAAGTGAACTGCCAATTGCAAAAGATGATGAGGAAATAATGGATTTGGTTGATCCTT   660
 G  S  E  L  P  I  A  K  D  D  E  E  I  M  D  L  V  D  P  S
CTGCTCCAGTGCCTGACTGGTTCACAGGAGAGGATCTTGCAAACTACGCATCTCTTTACG   720
 A  P  V  P  D  W  F  T  G  E  D  L  A  N  Y  A  S  L  Y  E
AAAAGTCAAGTTTCCGAACAGCATTGCAGGTGCCTTACAGGGCTTGGCTAGAAGAATATG   780
 K  S  S  F  R  T  A  L  Q  V  P  Y  R  A  W  L  E  E  Y  G
GAGTTAAAGATATCAAAGTCAAGGTTCCCTGTTTGCTTGTAATGGGAGAGAAGGATTACG   840
 V  K  D  I  K  V  K  V  P  C  L  L  V  M  G  E  K  D  Y  A
CCCTTAAATTTGGTGGATTAGAGCAATACGTTAAAAGTGGAATGGTGAAAGAATATGTGC   900
 L  K  F  G  G  L  E  Q  Y  V  K  S  G  M  V  K  E  Y  V  P
CTAATCTGGAAACCATATTCTTACCAGAAGGCAGTCATTTTGTACAAGAGCAGTTTCCTG   960
 N  L  E  T  I  F  L  P  E  G  S  H  F  V  Q  E  Q  F  P  E
AACAGGTCAATCAGTTGATTATCACCTTCCTCAAAAAGCTCATATAATAAACTGCTTGCC  1020
 Q  V  N  Q  L  I  I  T  F  L  K  K  L  I  *
AGCGACGTTGAATAAAGGGCAACCCAGTGCACGAAACTCCCGTTATGCACAAGGTTTGGG  1080
AGGAGCCGGCATTTGGGTCTTATTTTTCAGAGTTGAATGTTGATCTCAGTTTTATCAAAC  1140
AATACCATATCACATTTTCGGCATATTTCTACTTGTATGTTGATCAATAAAAGGGACGAT  1200
GGTTTACGCGCCTCAGTTCTAAAAAAAAAAAAAAAAAA                        1238
```

Fig. 6B

```
GTCCTACTCCATATCTCATCTTCTTTTCTCTGTTAGCGCGGAGTTAGGGACGCTAGGGGT
TCATCGTCAGAATCTTTTCGTCAGAAAATTACACTCTATATATATGCAG
```

Figure 7

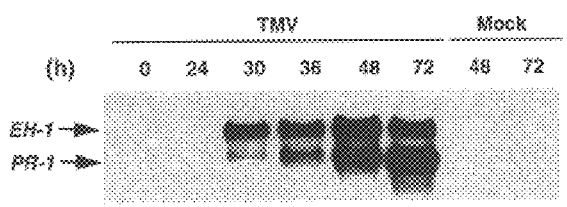
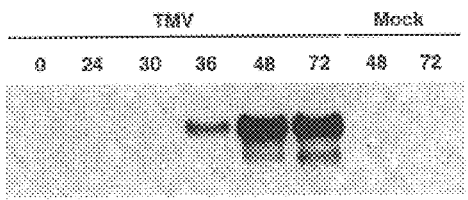
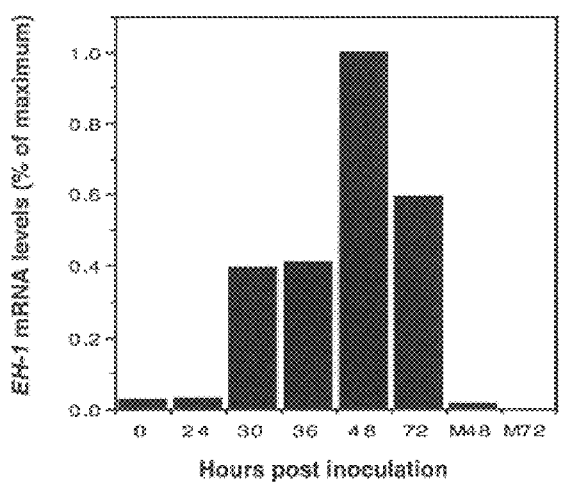
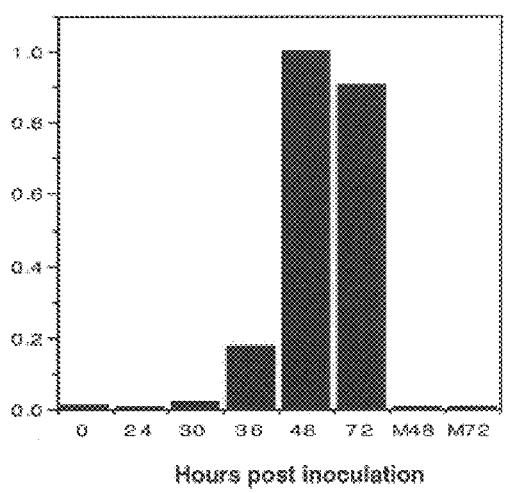
Figure 9

Fig. 10A
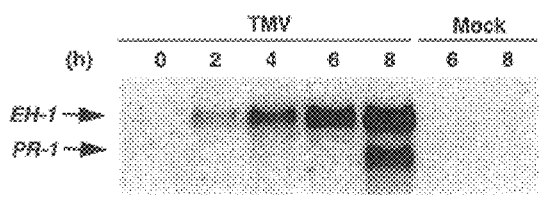
Fig. 10C
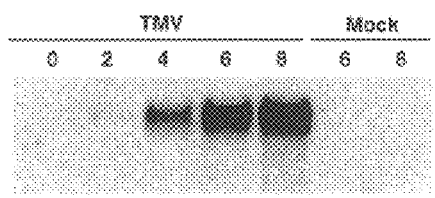
Fig. 10B
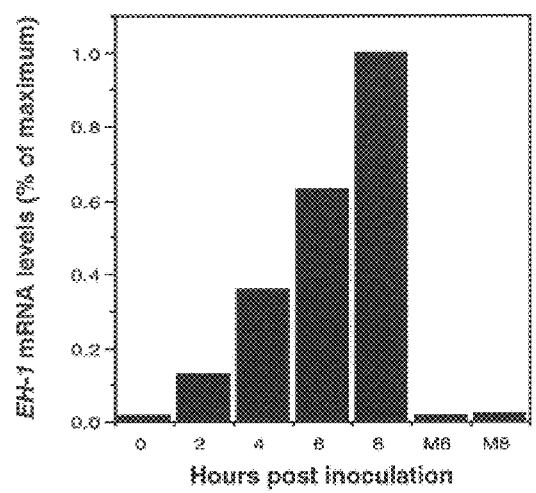
Fig. 10D
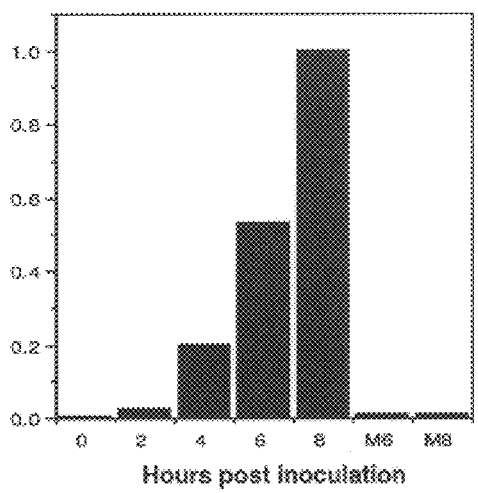
Figure 10

Fig. 11A
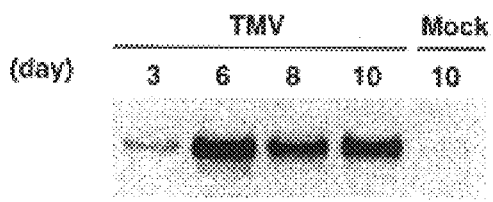
Fig. 11C
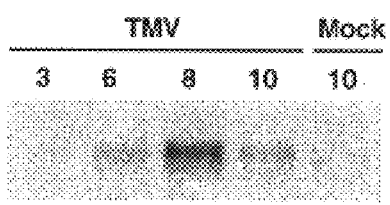
Fig. 11B
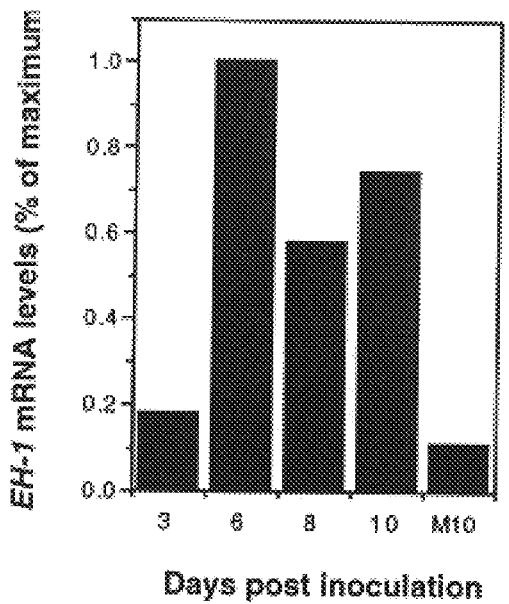
Fig. 11D
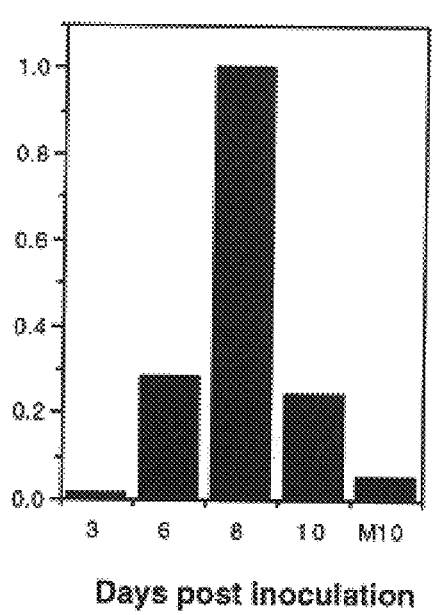
Figure 11

Fig. 12A
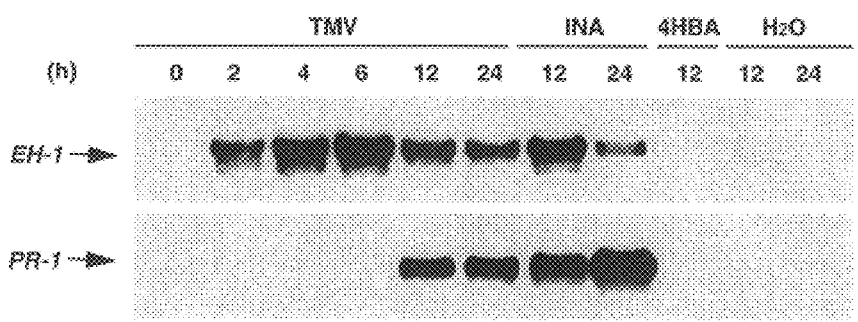
Fig. 12B
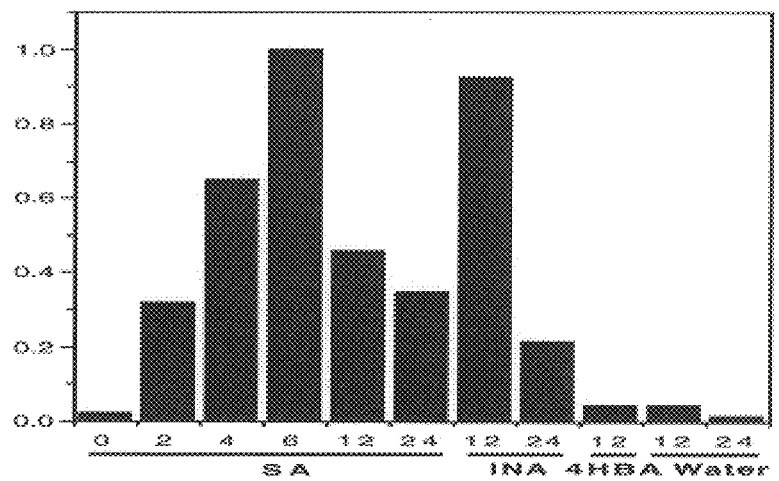
Fig. 12C
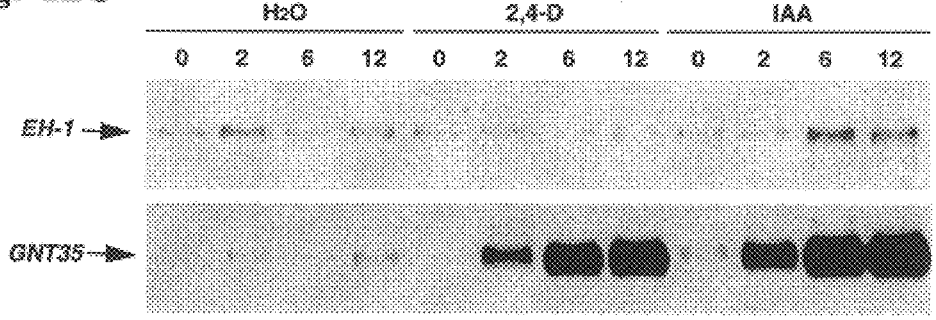
Figure 12

METHODS AND COMPOSITIONS FOR IMPROVING SALICYLIC ACID-INDEPENDENT SYSTEMIC ACQUIRED DISEASE RESISTANCE IN PLANTS

CROSS REFERENCE TO RELATED APPLICATION

This application claims priority to U.S. Provisional application Ser. No. 60/024,033, filed Aug. 12, 1996.

Pursuant to 35 U.S.C. §202(c) it is acknowledged that the U.S. Government has certain rights in the invention described herein, which was made in part with funds from the National Science Foundation, Grant Number MCB-9320371.

FIELD OF THE INVENTION

The present invention pertains to the fields of plant molecular biology. More specifically, the invention relates to induction of systemic acquired disease resistance in plants involving a novel salicylic acid-independent signal transduction pathway whose activation is associated with enhancement of a plant's ability to resist microbial infection.

BACKGROUND OF THE INVENTION

Several publications are referenced in this application in parentheses in order to more fully describe the state of the art to which this invention pertains. Full citations for these references are found at the end of the specification. The disclosure of each of these publications is incorporated by reference herein.

In plants, resistance to environmental challenges, e.g. pathogens, insects and stresses, enables them to better survive in nature, Resistance to pathogen attack is often associated with the hypersensitive response (HR), in which rapid, local cell death occurs at the infection site. The formation of these necrotic lesions is associated with the restriction of pathogen multiplication and spread. In the tobacco/tobacco mosaic virus (TMV) system, a typical HR develops on TMV-inoculated leaves of the tobacco cultivar Xanthi nc, which contains the N resistance gene. By contrast, when the TMV-susceptible cultivar Xanthi is infected, the virus spreads throughout the plant and causes disease symptoms. Several days after HR formation, systemic acquired resistance (SAR) develops throughout the plant (Ross, 1961a, 1961b; Ryals et al., 1994, 1996). SAR confers enhanced resistance not only to a secondary challenge by the initial infecting pathogen, but also to a broad range of other pathogens. Therefore, plant disease resistance is associated with both local (HR) and systemic (SAR) responses.

Activation of resistance responses is associated with the induction of a large number of defense genes and the synthesis of many secondary compounds. The former include genes encoding peroxidases, glucanases, chitinases, and other pathogenesis-related (PR) proteins while the latter include phytoalexins, phenolic compounds and lignin (Bowles, 1990; Cutt and Klessig, 1992). Phytoalexins are low molecular weight antimicrobial compounds that are synthesized by the plant and accumulate at the site of infection. While most phytoalexins are synthesized via the phenylpropanoid pathway, some are synthesized by the isoprenoid biosynthetic pathway (Ebel, 1986). Phenylalanine ammonia-lyase (PAL) is the first enzyme in the phenylpropanoid pathway and it regulates the biosynthesis of flavonoids, phytoalexins and lignins (Hahlbrock and Scheel, 1989; Dixon and Lamb, 1990). Levels of PAL mRNA and enzymatic activity increase in the inoculated tissue of resistant plants after pathogen infection. In addition, when tobacco plants are treated with a fungal elicitor, PAL mRNA accumulates in stem tissues (Pellegrini et al., 1994).

Plants resisting pathogen attack also synthesize a variety of PR proteins (Linthorst, 1991; Cutt and Klessig, 1992). In tobacco, at least five families of PR genes have been identified. They are induced in both the TMV-infected leaves and the upper uninoculated leaves of resistant cultivars (Ward et al., 1991). The function of some PR proteins is still unclear; however, several have been shown to have antimicrobial activities either in vivo or in vitro (Dempsey and Klessig, 1995).

Increases in salicylic acid (SA) levels also correlate with resistance to pathogen attack (Malamy et al., 1990; Metraux et al., 1990; Rasmussen et al., 1991). In tobacco resisting TMV infection, endogenous SA levels increase in both inoculated and uninoculated leaves. These increases correlate with the HR and SAR and precede the induction of PR genes (Malamy et al., 1990). A correlation between SA accumulation and resistance to pathogen attack has also been shown in other plants, e.g. cucumber and Arabidopsis (Metraux et al., 1990; Rasmussen et al., 1991; Uknes et al., 1993; Lawton et al., 1994; Summermatter et al., 1995; Dempsey et al., 1997). In addition, exogenously applied SA enhances resistance and induces nine gene families whose expression is associated with SAR in TMV-inoculated tobacco (Ward et al., 1991). Elevated SA levels also correlate with the activation of plant defenses in temperature shifted tobacco. At temperatures above 28° C., development of resistance to TMV is blocked and tobacco plants become systemically infected (Kassanis, 1952). At this elevated temperature, there is no detectable increase in SA levels, no PR protein synthesis and no HER after TMV infection (Gianinazzi, 1970; Yalpani et al., 1991; Malamy et al., 1992). However, when these infected tobacco plants are shifted to lower temperatures, resistance to TMV is restored. Moreover, a rapid and dramatic increase in SA levels precedes both PR gene expression and the appearance of a HR (Malamy et al., 1992).

Mutant analysis in Arabidopsis also provides support for SA's importance in disease resistance. Several mutants (e.g. npr1, nim1, and sai1), have been isolated which are unable to activate PR gene expression after treatment with SA or INA (2,6-dichloroisonicotinic acid, a synthetic functional analog of SA; Conrath et al., 1995; Durner and Klessig, 1995; Vernooij et al., 1995; Malamy et al., 1996). These mutants show greater susceptibility to bacterial and fungal pathogens (Cao et al., 1994; Delaney et al., 1995; Shah et al., 1997). conversely, mutants with elevated levels of SA, including the lesion mimic mutants acd2 and the 1sd series (Dietrich et al., 1994; Greenberg et al., 1994), as well as cpr1 (Bowling et al., 1994) and cep1 (Klessig et al., 1996), constitutively express these PR genes and exhibit enhanced resistance to pathogens.

Some of the strongest evidence supporting a signaling role for SA comes from the analysis of transgenic tobacco and Arabidopsis plants that contain the bacterial nahG gene encoding salicylate hydroxylase. Since salicylate hydroxylase degrades SA, these transgenic NahG plants are unable to accumulate SA. Following inoculation with TMV, NahG tobacco plants exhibit substantially reduced induction of PR gene expression and fail to develop SAR. Furthermore, they show enhanced susceptibility to infection with both virulent and avirulent pathogens (Gaffney et al., 1993; Delaney et al., 1994; Vernooij et al., 1994). Thus, SA appears to be required for an effective resistance response.

While SA mediates resistance to certain pathogens, other signal transduction pathways also appear to be involved in plant defense response. Both ethylene and jasmonates have been implicated as signal molecules that induce PR proteins during plant defense responses (Boller et al., 1983; Boller, 1991; Xu et al., 1994). Furthermore, several recent reports have shown that induction of a number of defense genes by pathogens, elicitors or abiotic agents (soluble sugars) is mediated by a SA-independent pathway(s) (Herbers et al., 1996; Penninckx et al., 1996; Pieterse et al., 1996; Vidal et al., 1997).

Compositions and methods that enhance disease resistance in plants are agronomically important and highly desirable. While SA is a key component in a plant's capacity to withstand environmental stresses, mounting evidence suggests that a second pathway leading to systemic acquired disease resistance exists. Thus, a need exists to identify and characterize the genes and encoded proteins involved in this novel, second pathway.

SUMMARY OF THE INVENTION

The present invention relates to a new signal transduction pathway in plants which is associated with and leads to the development of systemic acquired resistance (SAR). Activation of this pathway results in the induction of a diverse group of genes which are expressed in both uninfected and infected tissues in a salicylic acid (SA)-independent manner. These genes are termed SIS for SA-independent systemically induced.

According to one aspect of the invention, a method for identifying SIS genes is provided. The method uses the following steps: (a) providing pairs of plants, each pair being of of equivalent species and variety, wherein one of the pair (the "SA+" plant) accumulates endogenous SA, and the other of the pair (the "SA-" plant) does not accumulate endogenous SA; (b) inoculating one pair of plants with a plant pathogen to which the plant variety responds by exhibiting SAR; (c) mock-inoculating another pair of plants; (d) identifying defense-related genes in the plants by detecting genes that are expressed in the inoculated plants but not in the mock-inoculated plants (the defense-related genes indentified in this manner include the SIS genes as well as other defense-related genes); and (e) identifying the SIS genes by detecting the defense-related genes expressed in the inoculated SA+ plant and the defense-related genes expressed in the inoculated SA- plant, the SIS genes being expressed in both the inoculated SA and SA plants, the other defense-related genes being expressed only in the inoculated SA+ plant. In a preferred embodiment, the pair of plants are tobacco of the variety Xanthi nc and the pathogen is TMV. The plant not accumulating SA expresses a nahG gene, resulting in conversion of SA to catechol.

According to another aspect of the invention, a method is provided for identifying compounds that activate an SI-SAR pathway in plants. The method has the following steps: (a) providing a first DNA construct in which a first reporter gene is operably linked to a SIS gene promoter; (b) providing a second DNA construct in which a second reporter gene is operably linked to a SA-inducible gene promoter, such as a PR-1 gene promoter; (c) transforming a plant with the first and second DNA constructs; (d) administering to the plant a test compound suspected of activating the SI-SAR pathway; and (e) detecting expression of the first and second reporter genes, expression of the first reporter gene and lack of expression of the second reporter gene being indicative of activation of the SI-SAR pathway by the test compound.

Another method for identifying compounds that activate an SI-SAR pathway in plants comprises the following steps: (a) providing a plant that does not accumulate endogenous SA; (b) transforming the plant with a DNA construct in which a reporter gene is operably linked to a SIS gene promoter; (c) administering to the plant a test compound suspected of activating the SI-SAR pathway; and (d) detecting expression of the reporter gene, the expression of the reporter gene being indicative of activation of the SI-SAR pathway by the test compound.

According to another aspect of the invention, a method is provided for enhancing SA-independent resistance of a plant to infection by a plant pathogen. The method comprises transforming the plant with a DNA construct having a coding region of at least one SIS gene operably linked to a constitutive promoter, causing the transformed plant to constitutively express the SIS gene, thereby conferring the enhanced resistance to the plant pathogen.

In another aspect of the invention, a method for isolating signaling components of the SI-SAR pathway in plants is provided. The method comprises: (a) transforming a plant with a DNA construct having a reporter gene coding sequence operably linked to a SIS gene promoter; (b) producing progeny of the transgenic plant that are homozygous for the transgene; (c) mutagenizing seeds of the progeny; (d) producing M2 progeny from the mutagenized seeds; (e) selecting individuals of the M2 progeny that desplay altered expression of the reporter transgene as compared with non-mutagenized plants; and (f) identifying mutations in the selected mutagenized plants that confer the altered expression of the reporter transgene, the mutations being associated with genes that: encode signaling components of the SA-SAR pathway.

According to another aspect of the present invention, an isolated nucleic acid molecule is provided that includes an open reading frame encoding a plant pathogen-inducible epoxide hydrolase (piEH). This nucleic acid represents one of the SIS genes identified in accordance with the invention. In a preferred embodiment, the nucleic acid encodes a piEH that is inducible in the absence of SA. In various embodiments of the invention, the nucleic acid is DNA, either cDNA or genomic DNA. In other embodiments, it is RNA. In a preferred embodiment, the nucleic acid encodes a tobacco piEH, preferably having an amino acid sequence which is greater than 40% homologous with Sequence I.D. No. 2, and most preferably comprises Sequence I.D. No. 2.

According to another aspect of the invention, an isolated nucleic acid molecule is provided, which has a sequence selected from the group consisting of: (a) Sequence I.D. No. 1; (b) an allelic variant of Sequence I.D. No. 1; (c) a natural mutant of Sequence I.D. No. 1; (d) a sequence hybridizing with part or all of a sequence complementary to Sequence I.D. No. 1 and encoding a polypeptide substantially the same as part or all of a polypeptide encoded by sequence I.D. No. 1; and (e) a sequence encoding part or all of a polypeptide having amino acid sequence I.D. No. 2.

Also provided in accordance with the invention are recombinant DNA molecules comprising the aforementioned nucleic acid molecules, operably linked to vectors for transforming plant cells. Also provided are plant cells transformed with those recombinant DNA molecules, and transgenic plants comprising those recombinant DNA molecules.

According to another aspect of the invention, an isolated plant pathogen-inducible epoxide hydrolase (piEH) is provided, the expression of which is inducible by inoculation of the plant with a pathogen, in the absence of salicylic acid. In a preferred embodiment, the piEH is of tobacco origin and is inducible by inoculation of tobacco with TMV. In preferred embodiments, the piEH has an amino acid sequence greater than 40% homologous to Sequence I.D. No. 2, and most preferably comprises Sequence I.D. No. 2.

According to another aspect of the invention, a polypeptide is provided, which is produced by expression of an isolated nucleic acid sequence selected from the group consisting of: (a) Sequence I.D. No. 1; (b) an allelic variant of Sequence I.D. No. 1; (c) a natural mutant of Sequence I.D. No. 1; (d) a sequence hybridizing with part or all of a sequence complementary to Sequence I.D. No. 1 and encoding a polypeptide substantially the same as part or all of a polypeptide encoded by sequence I.D. No. 1; and (e) a sequence encoding part or all of a polypeptide having amino acid sequence I.D. No. 2.

In another aspect of the invention, antibodies immunologically specific for part or all of the aforementioned proteins are provided.

Other aspects and advantages of the invention will be understood by reference to the detailed description of the invention and examples set forth below.

BRIEF DESCRIPTION OF THE DRAWINGS

FIG. 1 shows kinetics of gene expression during TMV infection of wild-type plants. Tobacco leaves were either TMV or mock inoculated. RNA was isolated from three plants for each time point. Ten $\mu$g of RNA was loaded in each lane. The rRNA probe was provided as a control for variability in sample loading and blotting. Although the probes for the different genes were of similar specific activity, the length of exposure of the autoradiograms varied from 4–24 h to optimize detection in FIGS. 1, 3, 4, and 5. As a result, the band intensities with different gene probes can not be used as a measure of the relative abundance of the different mRNAs. The entire experiment with all ten probes was done twice. FIG. 1A: plants were incubated at 22° C. and samples were harvested at 24-h intervals after inoculation. FIG. 1B: plants were incubated at 32° C. for 48 h after inoculation and then shifted to 22° C. Leaves were harvested at the times indicated after plants were shifted to 22° C.

FIG. 3 shows kinetics of gene expression after TMV infection of NahG plants. Leaves from transgenic NahG plants were either TMV or mock inoculated. Ten $\mu$g of RNA, isolated from two plants at each time point, was loaded in each lane. The northern blots shown in FIGS. 1 and 3 were simultaneously hybridized with the same probes and exposed for the same length of time so the results can be directly compared between infected wild-type and NahG plants. This experiment with ten probes was done twice.

FIG. 3A: inoculated plants were incubated at 22° C. and samples were harvested at 24-h intervals. FIG. 3B: inoculated plants were incubated at 32° C. for 48 h and then shifted to 22° C. Leaves were harvested at the times indicated after plants were shifted to 22° C.

FIG. 5 shows kinetics of gene expression in upper uninoculated leaves. RNA was extracted from upper uninoculated leaves of TMV- or mock-inoculated plants at the times indicated in days post inoculation. Each time point represents RNA isolated from two plants. Ten $\mu$g of RNA was loaded in each lane and the experiment with all ten probes was done twice. FIG. 5A: wild-type plants; FIG. 5B: NahG plants (exposures of the autoradiograms were for the same length of times as in FIG. 5A except where noted: * exposure times in FIG. 5B were 5× longer than those in FIG. 5A; ** exposure time in FIG. 5B was 18× longer than that in FIG. 5A.

FIG. 6 shows the nucleotide and deduced amino acid sequences of the EH-1 cDNA. FIG. 6A: the nucleic acid sequence (Sequence I.D. No. 1) is presented on the top line and the derived one-letter amino acid sequence (Sequence I.D. No. 2) is shown below. The underlined letters indicate the positions of the initiation and the termination codons. The arrow in the nucleic acid sequence indicates the position of the splice junction. The accession number is U57350. FIG. 6B: the nucleic acid sequence (Sequence I.D. No. 3) of the splice of the intron corresponding to the partially spliced version of the EH-1 cDNA.

FIG. 7 shows a comparison of the amino acid sequences of tobacco (Sequence I.D. No. 2), potato (Sequence I.D. No. 4), Arabidopsis (Sequence I.D. No. 5), rat (Sequence I.D. No. 6) and human (Sequence I.D. No. 7) EHs. Shaded regions indicate identical (black) or similar (grey) amino acids of EH-1 and other EHs.

FIG. 9 shows kinetics of EH-1 and PR-1 gene expression in TMV-infected tobacco plants maintained at 22° C. Total RNA was isolated from TMV- or mock-inoculated leaves of wild-type (Xanthi nc) plants (FIG. 9A) or NahG plants (FIG. 9C). Ten Atg RNA was loaded in each lane.

FIGS. 9B and 9D show quantification of EH-1 transcripts corresponding to the data from FIGS. 9A and 9C, respectively. Since the scales in FIGS. 9B and 9D are relative, they cannot be directly compared. Accumulation of mRNA levels were quantified with a Phosphorimager. Induction levels were calculated by setting the maximum value to 1. The experiment was done twice.

FIG. 10 shows kinetics of EH-1 expression in TMV-infected tobacco plants after a temperature shift. Inoculated wild-type plants (FIG. 10A) and NahG plants (FIG. 10C) were incubated and maintained at 32° C. for 48 h before shifting to 22° C. Leaves were harvested at 2 h intervals starting at the time plants were shifted to 22° C. Ten $\mu$g RNA was loaded in each lane. FIGS. 10B and 10D show quantification of EH-1 transcripts corresponding to the data from FIGS. 10A and 10C. The method of quantification is described in FIG. 9. The experiment was done twice.

FIG. 11 shows kinetics of EH-1 expression in the upper, uninoculated leaves of TMV-infected tobacco. Total RNA was isolated from upper uninoculated leaves of wild-type plants (FIG. 11A) and NahG plants (FIG. 11C) at 3, 6, 8 and 10 days after TMV or mock inoculation. Ten $\mu$g of RNA was loaded in each lane. FIGS. 11B and 11D show quantification of EH-1 transcripts corresponding to the data from FIGS. 11A and 11C. The method of quantification is described in FIG. 9. The experiments were done at least twice.

FIG. 12 shows EH-1 gene expression in tobacco plants or suspension cells following treatment with different chemicals. FIG. 12A: tobacco leaves were injected with water or 1 mM SA, INA or 4HBA. Samples were harvested at the times indicated and total RNA was extracted from treated tissue. Ten $\mu$g of RNA was loaded in each lane. FIG. 12B: quantification of EH-1 transcripts corresponding to the data from FIG. 12A. The method of quantification is described in FIG. 9. The experiments were done twice. FIG. 12C: cell cultures were subcultured for 2 days in hormone-free medium to deplete hormones. Water, 2,4-D or IAA were then added to the media at 100 $\mu$M. Cells were collected at the times indicated.

DETAILED DESCRIPTION OF THE INVENTION

I. Definitions

Figure 2:
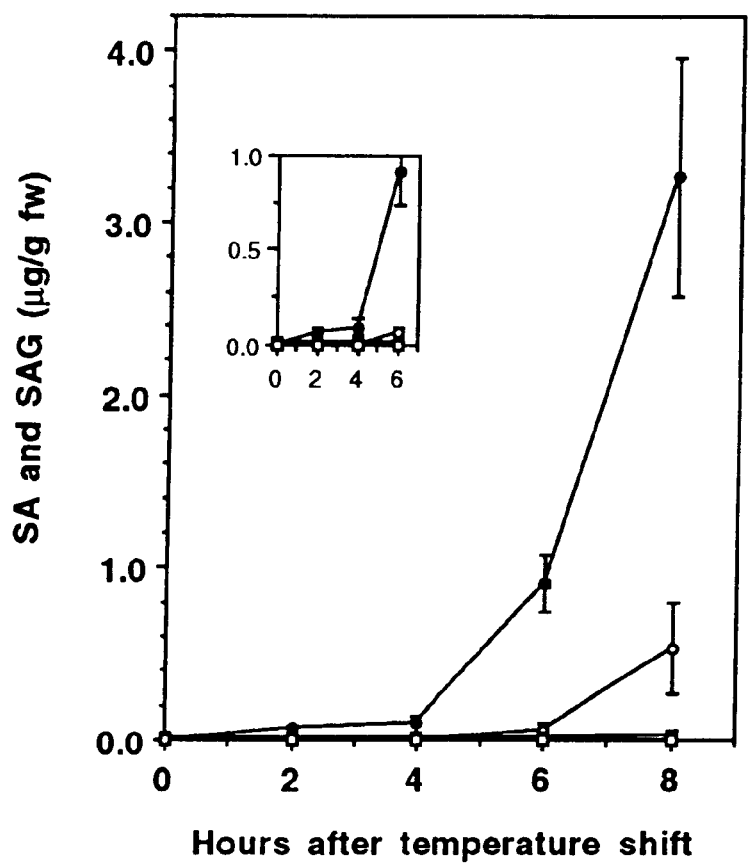
FIG. 2 shows kinetics of SA and SAG accumulation in TMV-infected leaves after the temperature shift. Plants were infected with TMV and incubated at 32° C. for 48 h before being shifted to 22° C. Inoculated leaves were harvested at the times indicated after the temperature shift, and the levels of SA (closed circle indicates wild-type; closed square indicates NahG) and SAG (open circle indicates wild-type; open square indicates NahG) were determined. Values are represented as $\mu$g/g fresh weight (fw). Each point and bar represents the mean±SD calculated from three samples obtained from three inoculated plants. Smaller changes in SA and SAG levels at early times can be seen in the insert with its expanded scale. The basal level of SA was ~0.02 $\mu$g/g of fw, while the level of SAG was often below the detectable limit of ~0.01 $\mu$g/g fw. The experiment was done twice.

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., SIP kinase), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "pathogen-inoculated" refers to the inoculation of a plant with a pathogen.

The term "disease defense response" refers to a change in metabolism, biosynthetic activity or gene expression that enhances the plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase (Dempsey and Klessig, 1995). Such defense responses appear to be induced in plants by several signal transduction pathways involving secondary defense signaling molecules produced in plants. Certain of these defense response pathways are SA dependent, while others are partially SA dependent and still others are SA independent, as described in detail elswhere herein. Agents that induce disease defense responses in plants include, but are not limited to: (1) microbial pathogens, such as fungi, bacteria and viruses; (2) microbial components and other defense response elicitors, such as proteins and protein fragments, small peptides, β-glucans, elicitins and harpins, cryptogein and oligosaccharides; and (3) secondary defense signaling molecules produced by the plant, such as SA, $H_2O_2$, ethylene and jasmonates.

The term "defense-related genes" refers to genes that are involved in the signal transduction pathways of a disease defense response. Defense-related genes may be involved in the disease defense response in several ways, such as by encoding proteins that regulate expression of other genes, or by encoding proteins involved in the biosynthesis of secondary defense signaling molecules or antimicrobial substances.

The term "promoter region" refers to the 5' regulatory regions of a gene. In the present invention, the use of CaMV 35S gene promoters and/or tetracycline repressor/operator gene promoters is contemplated.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Description of the SA-Independent SAR signal transduction pathway

One aspect of the present invention relates to the discovery of a new signal transduction pathway in plants which is associated with and leads to the development of SAR. Thus, the genes responsible for SI-SAR are induced in response to pathogens in both uninfected tissues as well as in infected tissue. Moreover, these genes are activated in a salicylic acid independent manner, although their expression can be induced transiently by exogenously applied SA. This class of genes has been designated with the acronym SIS which stands for SA-independent systemically induced and the corresponding pathway is referred to as the SA-independent (SI)-SAR pathway.

After differentially screening a cDNA library synthesized from temperature-shifted tobacco plants, seven groups of TMV-induced sis genes were isolated: ACCO (encoding 1-aminocyclopropane-1-carboxylate [ACC] oxidase), ACCD (encoding ACC deaminase), HIMGR (encoding 3-hydroxy-3-methylglutaryl-coenzyme A [HMG-CoA] reductase), APX (encoding ascorbate peroxtdase), one member of the acidic chitinase family (PR-3), five members of the SAR-associated SAR8.2 gene family (Alexander et al., 1992) and one member of the PAR-1 (photoassimilate responsive) gene family (Herbers et al., 1995). Most of the SIS genes encode a wide diversity of enzymes that are associated with growth, development, oxidative stress, and defense responses in tobacco. However, the function of the proteins encoded by two groups of SIS genes (SAR8.2 and PAR-1) is currently unknown.

Previous reports have shown that several of these SIS genes are induced in tobacco after TMV infection. These include: (1) HMGR (Genschik et al., 1992), which is a key enzyme regulating the production of isoprenoid derivatives; (2) acidic chitinase, which may provide an antimicrobial function by hydrolyzing fungal cell walls (Payne et al., 1990); and (3) ACCO, which catalyzes ethylene production (Knoester et al., 1995).

The induction of two groups of SIS genes identified by our screen has not previously been observed in tobacco plants after TMV infection. These include ACCD, which may regulate ethylene levels by converting ACC, the immediate precursor of ethylene, to ammonia and a-ketobutyrate (Honma and Shimomura, 1978); and a cytosolic APX (Orvar and Ellis, 1995). APXs are major hydrogen peroxide-scavenging enzymes in plants. They are involved in protecting plants from oxidative damage and are induced by environmental stresses, such as ozone (Conklin and Last, 1995) and drought (Van Rensburg and Krüger, 1994), as well as after pathogen attack in tomato (De Tullio and Arrigoni, 1992). The enhanced accumulation of APX transcripts after TMV infection suggests that APX may have a role in protecting plant cells from HR-associated oxidative stress.

The last two groups of SIS genes identified by our screen have no reported function. The SAR8.2 family was previously shown to be induced both locally and systemically in TMV-inoculated tobacco (Alexander et al., 1992). In contrast, the PAR-1 genes were initially identified in tobacco whose leaves accumulated high levels of soluble sugars due to the expression of a bacterial pyrophosphatase transgene (Herbers et al., 1995). Two members of the PAR-1 gene family, PAR-1a and c, were also detected in the inoculated and uninoculated leaves of tobacco undergoing systemic infection by potato virus Y, while PAR-1b was not induced. However, initial and subsequent screens of the TMV-infected library yielded only PAR-1b clones, suggesting that this may be the only member of the PAR-1 gene family induced during a resistance response to TMV.

While these seven groups of SIS genes encode unrelated proteins, their induction kinetics are very similar to each other and different from those associated with the well characterized PR proteins and phytoalexin biosynthetic enzymes such as PR-1 and PAL, respectively. All of the SIS genes are specifically induced in TMV resistant but not susceptible tobacco. Moreover, their activation is more rapid than that of PR-1 or PAL after temperature shifting TNV-inoculated tobacco from 32° C. to 22° C. Transcript levels of these seven groups, with the exception of chitinase, also reach maximal levels at earlier times than those of PR-1. It is possible that the sustained increase in PR-3 transcripts reflects the induction kinetics of this particular SIS gene. Alternatively, it might be caused by cross hybridization, since this gene shares significant homology with another acidic class II chitinase (PR-3) and the basic class I chitinases (Payne et al., 1990).

Additional differences between the induction of the SIS genes and that of either PR-1 or PAL are apparent in tobacco treated with exogenous SA or INA. SA or INA treatment causes a rapid and transient activation of six of the seven groups of SIS genes, whereas induction of the PR-1 genes is slow and sustained. In contrast, neither SA nor INA can induce PAL gene expression.

Thus, the SIS genes appear to be induced via a SA-independent pathway, in contrast to the PR-1 genes, whose expression is SA dependent. In temperature-shifted tobacco, SIS gene activation occurs prior to significant elevations in SA or SAG levels, whereas PR-1 gene induction occurs in tandem with SA accumulation. Furthermore, all seven groups of SIS genes are induced in the TMV-infected leaves of NahG tobacco. In contrast, very little to no PR-1 gene expression is detected in these leaves at concomitant times following inoculation, regardless of whether the plants are inoculated at 22° C. or temperature shifted. The SIS genes are also induced in the uninoculated, systemic leaves of TMV-infected NahG tobacco plants. The expression of ACCO, ACCD and APX is similar in the systemic leaves of both NahG and wild-type plants; however, the induction kinetics of the HMGR, PR-3, SAR8.2 and PAR-1 groups are delayed and considerably weaker in the NahG plants. In contrast, no PR-1 gene expression is detectable in the systemic leaves of NahG plants. These findings indicate that all of the SIS genes can be induced in the absence of SA accumulation; however, some are activated via a totally SA-independent pathway, while the induction of others is only partially SA independent.

In addition to the SIS genes described here, several recent reports have suggested that a SA-independent pathway(s) can mediate defense gene expression and disease resistance. Several Arabidopsis mutants have been identified that fail to express PR genes after treatment with exogenous SA (npr1–2, npr1–3, and sail; Glazebrook et al., 1996;Shah et al., 1997). Despite their inability to respond to SA, PR gene expression can be induced to varying extents in these mutants by inoculation with avirulent pathogens. In addition, a biocontrol strain of Pseudomonas fluorescens was shown to induce systemic resistance equally well in wild-type and transgenic NahG Arabidopsis plants (Pieterse et al., 1996). Similarly, the systemic induction of an Arabidopsis defensin gene after infection with the fungus *Alternaria brassicola* and the systemic expression of several tobacco PR (basic glucanase and chitinase) genes after treatment with *Erwinia caratovora* -derived elicitors were unaffected by the presence of the nahG gene (Penninckx et al., 1996; Vidal et al., 1997). Additionally, none of these defense genes was induced by SA treatment (Penninckx et al., 1996; Vidal et al., 1997). Strikingly, SA was observed to antagonize the elicitor-induced expression of the two tobacco basic PR genes, while the SA-mediated induction of PR-1 was inhibited by the Erwinia elicitors (Vidal et al., 1997). It has also been demonstrated that a number of tobacco defense-related genes (PR-Q and PAR-1) can be induced by elevated levels of soluble sugars; their sugar-induced expression, however, is not associated with changes in SA levels (Herbers et al., 1996).

Thus, various pathogens and elicitors can induce defense gene expression through SA-independent signaling pathways (Herbers et al., 1996; Penninckx et al., 1996; Pieterse et al., 1996; Vidal et al., 1997), but they clearly are not all the same. For instance, none of aforementioned plant-microbe systems in which defense gene expression was activated represent a race-specific resistance interaction; that is, the inducers used were virulent pathogens, a biocontrol bacterium or an elicitor. In contrast, the SA-independent induction of the SIS genes is mediated by a race-specific resistant interaction. Only tobacco plants carrying the N resistance gene, which also regulates the HR and a variety of SA-dependent defense responses, exhibit increases in SIS gene expression after TMV inoculation. Additional analyses of the SIS gene induction pathway should therefore provide novel mechanisms for manipulating SA-dependent and -independent defense responses. This is further underscored by the observation that both the SIS and PR-1 genes are activated by TMV infection and SA treatment. Thus, while the induction kinetics of these two groups of genes are substantially different, their respective signaling pathways appear to re-enforce each other. For example, the SA-independent pathway may play a secondary role in inducing PR gene expression, since PR genes can be induced in SA-insensitive mutant Arabidopsis after pathogen infection, although only to low levels in some cases (Glazebrook et al., 1996; Shah et al., 1997). Furthermore, the ability of exogenous SA to transiently induce SIS gene expression and the reduced induction of a subset of the SIS genes in systemic uninoculated leaves of TMV-infected NahG verses wild-type tobacco indicates that these genes may be synergistically induced by both SA-independent and -dependent pathways after pathogen infection. In contrast, expression of several of the SA-independent defense genes heretofore identified are not induced by SA (e.g. defensin; Penninckx et al., 1996) but can actually be suppressed by it (e.g. a basic glucanase and a basic chitinase; Vidal et al., 1997).

Example 1 describes how to identify components that induce SI-SAR. Examples 1 and 2 discuss in detail several classes of genes identified by the strategy set forth in Example 1. The sections below describe how these methods can be used to improve plant disease resistance via the novel SI-SAR pathway.

A. Screening compounds that activate the SI-SAR pathway

The protocols set forth in Example 1 enable the identification of novel compounds that induce the SI-SAR pathway as well as any as yet unidentified genes in or at the end of the pathway. Construction of transgenic plants that constitutively or inducibly express SIS genes or signaling components of the SI-SAR pathway would create plants with enhanced disease resistance.

Several methods are available to introduce DNA into plants and are well known to those skilled in the art of the construction of transgenic plants. These methods include, but are not limited to, Agrobacterium vectors, polyethylene glycol (PEG) treatment of protoplasts, bombardment of cells or tissues with microprojectiles coated with the transforming DNA (sometimes referred to herein as "biolistic DNA delivery") and temporary holes cut by a UV laser microbeam. Other methods include use of geminivirus vectors, calcium phosphate treatment of protoplasts, electroporation of isolated protoplasts and agitation of cell suspensions with microbeads coated with the transforming DNA. In an alternative embodiment, useful in plant systems where protoplasts may be obtained and regenerated into intact plants, plastid transformation may be achieved by polyethylene glycol (PEG) treatment of protoplasts in the presence of the transforming DNA. Methods for stable transformation in PEG-treated tobacco protoplasts, in accordance with methods of the present invention, are described by Golds et al., Bio/Technology, 11: 95–97 (January, 1993).

Promoters of one or more of the SIS genes, such as PAR-1, chitinase, or epoxide hydrolase can be used to control expression of selectable marker or reporter genes. Candidate marker or reporter genes include uidA (GUS), green fluorescent protein (GFP; aequorin) and bar (the streptomyces phosph-inothricin acetyl transferase gene which confers resistance to the herbicide phosphinothricin).

Transgenic *Arabidopsis thaliana* or tobacco plants carrying these gene constructs can be used to screen compounds for their ability to induce the SI-SAR pathway. For example, transgenic plants containing a PAR-1 promoter:GFP open reading frame (ORF) chimeric gene should fluoresce strongly after treatment with a compound that has the ability to induce this pathway. Alternatively, plants containing the PAR-1:bar transgene should be resistant to phosphincthricin after treatment with a compound that induces this pathway. Compounds which fail to induce this transgene will not protect the plant against phosphinothricin. Compounds will be administered to plants using methods described in the literature for the administration of SA and INA including spraying, watering or injection.

Since many of these SIS genes can also be activated at least transiently by SA, a counter screen can be used to eliminate compounds which induce SIS genes through SA. A candidate counter screen is based on the GUS (uidA) gene or the GFP gene, under control of the predominantly SA-inducible PR-1 gene promoter. Using this method, compounds are identified that activate the PAR-1:GFP reporter gene construct but not the PR-1:GUS reporter gene. A simple biochemical assay or histochemical staining procedure is available to monitor induction of the GUS reporter gene. However, it should be noted that if the SI-SAR pathway and the SA-dependent SAR pathway are parallel but contain one or more common upstream steps, then compounds may be identified which induce both pathways through their effects on the common step(s). The screening procedures can then be modified as more information becomes available.

B. Identification of as-yet unidentified signaling components of the SI-SAR pathway The transgenic plants described above can also be used to identify additional signaling components of the SI-SAR pathway. This approach involves identification of mutants which have altered expression of the SI-SAR genes but not of the SA-dependent SAR genes such as PR-1. If, as discussed above, the two pathways share upstream steps, then such screening methods will also identify genes that are expressed in both pathways. Thus again, the screens may be modified accordingly. The experiments to identify relevant genes can be performed using *Arabidopsis thaliana*, the plant of choice for genetic analysis.

To identify mutants that constitutively express the SIS genes, several approaches can be taken. Screening of the Feldman and Koncz T-DNA insertional mutant libraries of *Arabidopsis thaliana* for mutants which constitutively express PR-1 gene, or cep mutants, is a preferred approach. Screening is performed using Northern analysis of RNA from pools of 20 plants. Several cep mutants have been identified by the present inventors. These same RNA blots can also be used to screen for mutants with activated PAR-1, chitinase or epoxide hydrolase genes. Identification of a pool which contains a positive signal is followed by identification of the individual plant constitutively expressing the gene of interest, e.g., the PAR-1 gene.

Transgenic plants can also be constructed which carry the PAR-1:bar (or PAR-1:GFP) transgene for selection and the PR-1:GFP (or PR-1:GUS) transgene for counter selection. The plants can then be mutagenized by standard protocols, EMS or T-DNA for example, and M2 seedlings selected for phosphinothricin resistance, conferred by the constitutive expression of the PAR-1:bar transgene in the mutants. These phosphinothricin-resistant mutants are then counter screened for those which do not fluoresce (or do not have high levels of GUS) because they do not express the SA-inducible PR genes constitutively.

These trangenic plants can then be employed to identify mutants that are defective in the activation of the SI-SAR pathway by pathogen infection. Initially, it is determined whether PAR-1 gene expression can be induced in the Arabidopsis ecotype transformed with the SIS:reporter gene by infection with avirulent strains of *Pseudomonas syringae* or *Peronospora parasitica*. Preferably, the Columbia (Col) 0 ecotype is utilized. PAR-1 gene expression would also be tested in Arabidopsis of the same ecotype which contains the nahG gene whose product destroys the SA signal. Once the suitable combination of avirulent pathogen and resistant ecotype that induces SIS genes such as PAR-1 in a SA-independent manner has been identified, this host ecotype is transformed with an appropriate reporter gene. For example, if P.s. pv tomato DC3000 (carrying the avr-Rpt2 gene), referred to hereafter as Pst, activates PAR-1 in Co10 and also in Col0 carrying the nahG gene, then M2 seedlings of the PAR-1:GFP transgenic Arabidopsis can be screened for mutants that lack fluorescence after Pst infection. Provided they also carried the PR-1:GUS reporter transgene, these seeds can be counter screened for the absence of elevated GUS activity after Pst infection.

Isolation of the mutated genes from the mutagenized plants giving rise to the mutant phenotype can be performed using MAP-based positional cloning techniques (Ausubel et al., 1997, supra). Physical markers flanking the mutated gene can be identified using standard mapping techniques with RFLP, CAPS, AFLP and microsatellite markers. YAC, BAC, or cosmid clones from a library made from non-mutant plants that span the regions between the closest markers on each side of the mutation are then used for transformation to complement the mutation and thereby identify the mutant gene.

C. Identification of new SIS genes

New SIS genes can also be identified and used to construct novel transgenic plants constitutively expressing these genes for enhanced resistance to disease. To identify these SIS genes, advantage will be taken of the NahG transgenic tobacco or Arabidopsis. Novel genes can be identified by their induction response to avirulent pathogens. For example, TMV infection of NahG transgenic *Nicotiana tabacum* cv Xanthi nc or Pst infection of NahG transgenic Arabidopsis ecotype Col 0 can be used. Two methods that can be utilized to identify those genes which are differentially expressed under the above conditions are: (1) differential screening of induced mRNA which was employed in this study and described in Example I; or (2) differential display (Llang and Pairdee (1992) Science 257:967–971). An alternative approach is to use, for infection, a pathogen whose ability to grow and spread in the host plant is not enhanced by expression of nahG gene in the host plant, that is, the avirulent phenotype is not lost in the NahG transgenic hosts.

A subtractive cDNA library may be prepared as follows: Mock-inoculated and pathogen-inoculated libraries are prepared as described in Example 1 and are in vivo excised according to standard in vivo excision protocols, such as those provided by Stratagene. Obtained bacterial colonies are amplified and their recombinant plasmid DNA isolated using standard procedures. 200 $\mu$g of the mock-inoculated plasmid cDNA library is digested with NotI while the pathogen inoculated cDNA library is cut with EcoRI. cDNA fragments are then separated in agarose gels and fragments between 0.5 kb and 1.5 kb eluted. Mock-inoculated cDNA is then photobiotinylated (Clontech) according to published procedures (Strauss; and Ausubel, (1990) Proc. Natl. Acad. Sci. USA 87:1889–1893). Photobiotinylated mock-inoculated cDNA and pathogen-inoculated cDNA are mixed in a ratio of 10:1, denatured at 95° C. and renatured by slowly decreasing the temperature to 25° C. Avidin (Vectrex Avidin) is added to the mixture and mock-inoculated and hybrid cDNA molecules removed by centrifugation. Pathogen-inoculated enriched cDNA fragments are then cloned in a a vector, packaged and transfected in suitable host cells, the titer determined and the substractive cDNA library obtained amplified.

D. Construction of transgenic plants that constitutively express one or more SIS genes or signaling components of the SI-SAR pathway involved in the induction of SIS genes Transgenic plants constitutively expressing one or more SIS genes can be generated. These plants are expected to have enhanced resistance to pathogens, as has been shown for transgenic plants expressing PR genes. One or more SIS genes can be placed under a powerful constitutive promoter like the Cauliflower Mosaic Virus (CaMV) 35S promoter and introduced into plants using established plant transformation procedures such as Agrobacterium-mediated transformation. Following identification and cloning of one or more genes encoding signaling components of the SI-SAR pathway (as described in B above), transgenic plants can also be constructed in which expression of this signaling component gene is altered. Expression is modified by ectopic overexpression of the gene under control of the CaMV 35S promoter. Expression can also be disrupted by the expression of the gene in an antisense orientation under the CaMV 35S promoter.

III. Novel epoxide hydrolase gene that is inducible independently of SA

Differential screening of a TMV-induced tobacco cDNA library identified a clone, designated EH-1, that exhibits approximately 35% sequence identity with the soluble EHs reported from both plant and mammalian systems (Beetham et al., 1993; Grant et al., 1993; Kiyosue et al., 1994; Knehr et al., 1993; Stapleton et al., 1994). The identification of EH-1 is described in detail in Example 2.

EH-1 transcripts accumulate in the inoculated, and upper, uninoculated leaves of tobacco plants resistant to TMV infection. In contrast, no induction of EH-1 expression is detected in TMV-susceptible plants. Strikingly, EH-1 transcripts also accumulate in the TMV-inoculated and systemic leaves of NahG tobacco plants, which are unable to accumulate SA. Thus, EH-1 induction after TMV infection appears to be mediated, at least in part, by a SA-independent pathway.

Further demonstrating that EH-1 is activated via a SA-independent pathway is the differences in expression kinetics of EH-1 and the defense-associated PR-1 genes, whose TMV-induced expression requires SA. EH-1 transcripts accumulate slightly more rapidly than those of PR-1 in the TMV-inoculated leaves of tobacco maintained solely at 22° C. and substantially quicker than PR-1 mRNAs after a temperature shift. For example, EH-1 was induced within 2 h after temperature shift while substantial increases in SA and PR-1 mRNA levels was not evident until 6 and 8 h, respectively (see Example 1). Thus, the induction kinetics of EH-1 are similar to those of the SIS genes described in Example 1.

While TMV-induced EH-1 expression occurs in the absence of SA accumulation, SA can positively modulate its expression. In the TMV-inoculated leaves of NahG plants, which fail to accumulate SA, EH-1 expression is delayed compared to that observed in wild-type plants and in the systemic leaves it was both delayed and weaker. Furthermore, EH-1 transcripts accumulate rapidly and transiently after treatment with either SA or INA, suggesting that its expression can be induced through a SA-dependent pathway as well as an SA-independent pathway. Surprisingly, EH-1 transcripts accumulated significantly more rapidly after SA treatment than those for PR-1. Thus, while SA can activate both genes, the pathways through which it does so appear to be different.

The function of EH in plants is less well defined than its function in animals; however, it is thought to play an important role in the biosynthesis of cuticular components (Pinot et al., 1992). The cuticle is composed of a variety of cutin monomers, which are hydroxy and epoxy fatty acids. The cuticle is the first line of defense against many microbes. Some pathogens break this physical barrier via production and secretion of cutinase (Kolattukudy, 1985), and thus the induction of EH may play an important role in strengthening and repairing the cuticle damage caused by pathogen attack.

A link between cutin biosynthesis and EH was established when it was shown that a purified EH from soybean synthesized a prevalent cutin monomer when supplied with the appropriate substrate (Blée and Schuber, 1992). More recently, it has been suggested that the products of the cloned sEH genes from Arabidopsis and potato are also involved in cutin biosynthesis, based on their expression patterns (Kiyosue et al., 1994; Stapleton et al., 1994). The correlation between the AtsEH gene product: and cutin synthesis was further strengthened by the observation that both AtsEH and a cytochrome P450 omega-hydroxylase, which belongs to a family of enzymes involved in cutin and suberin biosynthesis; (Kolattukudy, 1980, 1981), are induced by auxin (Salaün et al., 1986; Kiyosue et al., 1994). In contrast, the tobacco EH-1 gene exhibited little or no induction after auxin treatment. Moreover, EH-1 is the only plant EH reported to be inducible by pathogen infection. Thus, it appears that EH-1 is a member of a novel and distinct class of genes encoding a type of EH that serves a different functions in plants than the EH proteins heretofore described. This new class of EH is referred to herein as "pathogen-inducible" EH ("piEH") and the gene(s) encoding piEH proteins are sometimes referred to herein as piEH genes. EH-1 is considered to be an exemplary member of this class.

A tobacco clone that encodes EH-1, an exemplary piEH of the invention, is described in detail herein. The nucleotide sequence of a cDNA encoding tobacco piEH is set forth in FIG. 6 as Sequence I.D. No. 1. It is believed that Sequence I.D. No. 1 constitutes a full-length piEH-encoding clone as it contains a suitable methionine for initiation of translation, with an open reading frame very similar in size to other plant cDNAs shown to encode functional EHs (see FIG. 7).

Although the tobacco piEH is described and exemplified herein, this invention is intended to encompass nucleic acid sequences and proteins from other species that are sufficiently similar to be used interchangeably with tobacco piEH-encoding nucleic acids and proteins for the purposes described below. Because of the conservation of specific key portions of genes encoding EHs, it will be appreciated by those skilled in the art that piEH-encoding nucleic acids from diverse species, and particularly higher plant species, should possess a sufficient degree of homology with tobacco piEH so as to be interchangeably useful in various applications. The present invention, therefore, is drawn to piEH nucleic acids and piEH proteins from any plant species in which they are found, preferably to piEHs of higher plant origin. Accordingly, when the term "piEH" is used herein, it is intended to encompass all piEHs falling within the confines of homology set forth below, of which the tobacco piEH encoded by EH-1 is an exemplary member.

Allelic variants and natural mutants of Sequence I.D. No. 1 are likely to exist within the plant genome and within the genomes of other species. Because such variants are expected to possess certain differences in nucleotide and amino acid sequence, this invention provides an isolated piEH nucleic acid molecule having at least about 50% (preferably 60% and more preferably over 70%) sequence homology in the coding region with the nucleotide sequence set forth as Sequence I.D. No. 1 (and, most preferably, specifically comprising the coding region of sequence I.D.

No. 1). This invention also provides an isolated piEH having at least about 40% (preferably 60% or greater) sequence homology with the amino acid sequence of Sequence I.D. No. 2. Because of the natural sequence variation likely to exist among piEHs and nucleic acids encoding them, one skilled in the art would expect to find up to about 50–60% nucleotide sequence variation, while still maintaining the unique properties of the piEH of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. its structure and/or biological activity). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide that do not affect structure or function. The terms "percent identity" and "percent similarity" are also used herein in comparisons among amino acid sequence. These terms are intended to be defined as they are in the UWGCG sequence analysis program (Devereaux et al., Nucl. Acids Res. 12:387–397, 1984), available from the University of Wisconsin.

The following description sets forth the general procedures involved in practicing this aspect of the present invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (1989) (hereinafter "Sambrook et al.") are used.

A. Preparation of piEH Nucleic Acid Molecules, piEH Protein and Antibodies Against piEH 1. Nucleic Acid Molecules Nucleic acid molecules encoding the piEH of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.24 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.24 kb double-stranded molecule. A synthetic DNA molecule so constructed may then be cloned and amplified in an appropriate vector.

Nucleic acid sequences encoding piEH may be isolated from appropriate biological sources using methods known in the art. In a preferred embodiment, a cDNA clone is isolated from a tobacco cDNA library. In an alternative embodiment, genomic clones encoding piEH may be isolated. Alternatively, cDNA or genomic clones encoding piEH from other species, preferably higher plant species, may be obtained.

In accordance with the present invention, nucleic acids having the appropriate level sequence homology with the coding region of Sequence I.D. No. 1 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 $\mu$g/ml denatured, fragmented salmon sperm DNA, 0.05% sodium pyrophosphate and up to 50% formamide. Hybridization is carried out at 37°–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45°–55° in 2×SSC and 0.1% SDS, changing the solution every 30 minutes.

Nucleic acids of the present invention may be maintained as DNA in any convenient cloning vector. In a preferred embodiment, clones are maintained in plasmid cloning/expression vector, such as PGEM-T (Promega Biotech, Madison, Wis.) or pBluescript (Stratagene, La Jolla, Calif.), either of which is propagated in a suitable E. coli host cell.

PiEH-encoding nucleic acid molecules of the invention include CDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting piEH genes or mRNA in test samples of plant tissue or other biological sources, e.g. by PCR amplification, or for the positive or negative regulation of expression of piEH genes at or before translation of the mRNA into proteins.

2. Proteins

A piEH protein of the present invention may be prepared in a variety of ways, according to known methods. The protein may be purified from appropriate sources, e.g., cultured plant cells or tissues.

Alternatively, the availability of nucleic acid molecules encoding piEH enables production of the protein using in vitro expression methods known in the art. For example, a CDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of piEH may be produced by expression in a suitable procaryotic or eucaryotic system. For example, part or all of a DNA molecule, such as the cDNA having Sequence I.D. No. 1, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The piEH produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The piEH of the invention, prepared by the aforementioned methods, may be analyzed according to standard procedures. Methods for analyzing the physical characteristics and biological activity of EHs are known in the art.

The present invention also provides antibodies capable of immunospecifically binding to proteins of the invention. Polyclonal or monoclonal antibodies directed toward piEH may be prepared according to standard methods. Monoclonal antibodies may be prepared according to general methods of Köhler and Milstein, following standard protocols. In a preferred embodiment, antibodies are prepared, which react immunospecifically with various epitopes of piEH.

Polyclonal or monoclonal antibodies that immunospecifically interact with piEH can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-piEH antibodies are described below.

B. Uses of piEH Nucleic Acids, piEH Protein and Antibodies

The potential of recombinant genetic engineering methods to enhance disease resistance in agronomically important plants has received considerable attention in recent years. Frotocols are currently available for the stable introduction of genes into plants, as well as for augmentation of gene expression. The present invention provides nucleic acid molecules which, upon stable introduction into a recipient plant, enhance the plant's ability to resist pathogen attack. piEH proteins of the invention may also be used as a research tool to identify other proteins involved in the hypersensitive response and/or systemic acquired resistance response in plants.

A. piEH-Encoding Nucleic Acids piEH-encoding nucleic acids may be used for a variety of purposes in accordance with the present invention. piEH-encoding DNA, RNA, or fragments thereof may be used as probes to detect the presence of and/or expression of genes encoding piEH. Methods in which piEH-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The piEH-encoding nucleic acids of the invention may also be utilized as probes to identify related genes either from plants or from other species. As is well known in the art, hybridization stringencies may be adjusted to allow hybridization of nucleic acid probes with complementary sequences of varying degrees of homology. Thus, piEH-encoding nucleic acids may be used to advantage to identify and characterize other genes of varying degrees of relation to p-iEH, thereby enabling further characterization the signalling cascade involved in the disease resistance response in plants. Additionally, they may be used to identify genes encoding proteins that interact with piEH (e.g., by the "interaction trap" technique as described, for example, by Golemis et al., Unit 20.1.1–20.1.28 in Current Protocols in Molecular Biology, eds. F. M. Ausubel et al., John Wiley & Sons, N.Y., 1996), which should further accelerate elucidation of these cellular signalling mechanisms.

Nucleic acid molecules, or fragments thereof, encoding piEH may also be utilized to control the production of piEH, thereby regulating the amount of protein available to participate in disease resistance signalling pathways. Alterations in the physiological amount of piEH may act synergistically with other agents used to protect plants during pathogen attack. In one embodiment, the nucleic acid molecules of the invention may be used to decrease expression of piEH in plant cells. In this embodiment, full-length antisense molecules are employed which are targeted to piEH, or antisense oligonucleotides, targeted to specific regions of piEH-encoding genes that are critical for gene expression, are used. The use of antisense molecules to decrease expression levels of a predetermined gene is known in the art. In a preferred embodiment, antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, overexpression of piEH is induced to generate a co-suppression effect. This excess expression serves to promote down-regulation of both endogenous and exogenous piEH-encoding genes. Under other circumstances, overexpression can lead to overproduction of piEH. overproduction of piEH in transgenic plants may be assessed by immunofluorescence or other standard techniques known in the art. Alternatively, overproduction of piEH in transgenic plants or plant cells may facilitate the isolation and characterization of other components involved in protein-protein complex formation occurring during the disease resistance response in plants.

As described above, piEH nucleic acids are also used to advantage to produce large quantities of substantially pure piEH protein, or selected portions thereof.

2. PiEH Protein and Antibodies

Purified piEH, or fragments thereof, may be used to produce polyclonal or monoclonal antibodies which also may serve as sensitive detection reagents for the presence and accumulation of piEH (or complexes containing piEH) in cultured plant cells or tissues and in intact plants. Recombinant techniques enable expression of fusion proteins containing part or all of the piEH protein. The full length protein or fragments of the protein may be used to advantage to generate an array of monoclonal or polyclonal antibodies specific for various epitopes of the protein, thereby providing even greater sensitivity for detection of the protein in cells or tissue.

Polyclonal or monoclonal antibodies immunologically specific for piEH may be used in a variety of assays designed to detect and quantitate the protein. Such assays include, but are not limited to: (1) flow cytometric analysis; (2) immunochemical localization of piEH in cultured cells or tissues; and (3) immunoblot analysis (e.g., dot blot, Western blot) of extracts from various cells and tissues. Additionally, as described above, anti-piEH can be used for purification of piEH (e.g., affinity column purification, immunoprecipitation).

3. Transgenic Plants

Transgenic plants constitutively expressing piEH genes can be generated using standard transformation methods known to those skilled in the art. Presumably, these plants will have altered resistance to pathogens as the piEH has been shown to be induced during a resistance response to TMV infection. The piEH gene can be placed under a powerful constitutive promoter and introduced into plants according to the methods described above for other SIS genes.

Transgenic plants expressing the piEH gene under an inducible promoter are also contemplated to be within the scope of the present invention. Inducible plant promoters include the tetracycline repressor/operator controlled promoter. Optionally, transgenic plants can be created containing mutations in the region encoding the active site of piEH.

From the foregoing discussion, it can be seen that piEH nucleic acids and piEH proteins and antibodies of the invention can be used to detect piEH gene expression and protein accumulation for purposes of assessing the genetic and protein interactions involved in the plant disease resistance response. It is also anticipated that piEH nucleic acid molecules and transgenic plants containing them will be useful for the regulation of the disease resistance pathway in plants and for enhancing resistance to plant pathogens. A brief discussion of the functions EH may fulfill in disease resistance is set forth below.

In addition to cutin biosynthesis, plant EH may help generate signals that activate defense responses after pathogen attack. A variety of plant pathogenic fungi hydrolyze plant cuticles and thereby release cutin monomers (Kolattukudy, 1985). Recently, it was demonstrated that several chemically synthesized cutin monomers can act as signals leading to acquired resistance in barley and rice (Schweizer et al., 1994; 1996a). Of the individual monomers tested, cis-9,10-epoxy-18-hydroxystearic acid (HESA), which is a major component of barley cutin, was the most effective at protecting a highly susceptible barley cultivar against attack by a fungal pathogen (Schweizer et al., 1996a). This epoxide cutin monomer also caused the rapid alkalinization of media by potato suspension cells (Schweizer et al., 1996b; Felix et al., 1993). Interestingly, HESA can be converted to 9,10,18-trihydroxystearic acid by the purified soybean EH (Blée and Schuber, 1993). This latter compound, while less toxic than HESA, was nearly as effective at inducing resistance to fungal infection in barley (Schweizer et al., 1996a). In addition, it induced media alkalinization in potato, although to a lesser extent than HESA (Schweizer et al., 1996b). Thus, EH may promote the induction of defense responses by converting highly toxic epoxide cutin monomers to less harmful compounds that signal the activation of certain defense responses.

EH may also play a role in detoxification of other harmful metabolites. sEH are conserved between plants and animals. In mammals, they are associated with the detoxification of xenobiotics. A role in detoxification might be particularly useful during the oxidative burst and associated HR in plants. EH may help protect plants from oxygen-based toxins produced at sites of infections. This potential protective function of EH might even help limit host cell death during the HR.

EHs may also affect the synthesis of jasmonic acid (JA). JA plays a key role in response to wounding and insect attack (Farmer and Ryan 1992; Reinbothe et al., 1994). In addition, there is an increase body of evidence suggesting its participation in defense responses to microbial pathogens (Reinbothe et al., 1994; Yang et al., 1997). JA is synthesized from linolenic acid via the octodecanoid (oxylipin) pathway (Vick and Zimmerman, 1983; Hamberg and Gardner, 1992). Linolenic acid can also be converted to epoxy fatty acids by peroxygenase. One of these epoxy fatty acids, cis-12,13-epoxy-9(Z)-octadecenoic acid, has recently been shown to be a strong inhibitor of allene oxide cyclase (Ziegler et al., 1997), a enzyme necessary for the conversion of linolenic acid to JA. Hydrolysis of the epoxy fatty acids to hydroxy fatty acids by EHs (Blée and Schuber, 1990; Hamberg and Hamberg, 1990) could prevent inhibition of JA production.

The following specific examples are provided to illustrate embodiments of the invention. They are not intended to limit the scope of the invention in any way.

EXAMPLE 1

Activation of a Diverse Set of Genes During the Tobacco Resistance Response to TMV that is Independent of Salicylic Acid and Distinct from the Induction of PR-1 Genes To gain additional insights into the pathway(s) through which defense responses were induced and to identify components of the signal transduction pathway(s) leading to resistance, we have isolated a variety of genes from a TMV-induced tobacco cDNA library. All of these genes were induced in both TMV-infected tissue, as well as upper uninoculated tissue. Surprisingly, these genes were also expressed equally well in TMV-infected leaves of NahG tobacco plants. Thus, they appear to be induced through a SA-independent pathway. Based on their kinetics of expression, these genes represent a different category from other previously characterized defense genes, such as those encoding PR proteins and phytoalexin biosynthetic enzymes. Therefore, we term them SIS genes for SA-independent systemically induced genes. However, expression in uninoculated leaves of a subset of these SIS genes was partially suppressed in NahG plants, suggesting that SA plays a role in regulating their expression in systemic tissue.

EXPERIMENTAL PROCEDURES

Plant material and inoculation

Tobacco (Nicotiana tabacum cv. Xanthi nc) plants and NahG-10 seeds, kindly provided by John Ryals at Novartis, Research Triangle, NC, were grown at 20° C. in a growth room with a 14-h day cycle. Two upper, fully expanded leaves of 6–8 week-old plants were infected with TMV strain U1 at a concentration of 1 μg/ml in 50 mM phosphate buffer (pH 7.2) containing carborundum. Control plants were treated with phosphate buffer and carborundum only. Inoculated plants were maintained in a 22° C. growth chamber until harvesting. In temperature shift experiments, plants were immediately put into a 32° C. growth chamber after infection with TMV. After a 48 h incubation period, the temperature was shifted from 32° C. to 22° C.

Chemical treatments

SA and its analog 4-hydroxybenzoic acid were purchased from Sigma. INA was provided by Uwe Conrath and Heinrich Kauss at Universitat Kaiserslautern, Germany. All chemicals were dissolved in water and adjusted a pH of 6.5 with NaOH. They were injected into plants at a concentration of 1 mM. Control plants were injected with distilled water.

cDNA library construction

The cDNA library was constructed from RNA extracted from 8 g of TMV-infected tobacco leaves at 4 h after the temperature shift. Poly(A) RNA was purified from total RNA with the Fast Track mRNA isolation kit (Invitrogen, San Diego, Calif.) according to manufacturer's instructions. The cDNA library was constructed using the ZAP Express™ cDNA synthesis kit (Stratagene, La Jolla, Calif.). The first cDNA strand was synthesized from 5 µg of Poly(A) mRNA with a poly(dT) primer containing a XhoI site. After second strand synthesis, the double-stranded cDNA was ligated to EcoRI adaptors. The cDNA was digested with XhoI, fractionated on a Sephacryl column, ligated to the ZAP Express vector arms, and packaged using Gigapack II Gold packaging extract. A library of $8 \times 10^6$ recombinants with insert sizes ranging from 500 bp to 4 kb was obtained.

Differential screening and Southern analysis

Approximately $5 \times 10^5$ recombinant phage were screened by standard differential screening methods (Sambrook et al., 1989). Duplicate filters (Duralon-UV from Strategene, La Jolla, Calif.; and Hybond-N from Amersham, Cleveland, Ohio) containing $5 \times 10^3$ recombinant plaques were screened. Probes were prepared from 1 µg of poly(A) RNA extracted from tobacco plants grown at 22° C. Leaves were harvested at 48 h after infection with TMV or treatment with buffer (mock). $^{32}$P-labeled probe was prepared according to Sambrook et al. (1989). Prehybridization and hybridization were performed in a solution containing 2×PIPES buffer (0.8M NaCl, 20 mM PIPES, pH 6.5), 50% formamide, 0.5% SDS and denatured salmon sperm DNA (100 Mg/ml) at 42° C. After secondary screening, the candidate clones were excised from the ZAP Express vector according to the manufacturer's protocol (Stratagene, La Jolla, Calif.). The positive clones were determined by Southern hybridization of two identical membranes with probes made from total mRNA isolated from TMV- or mock-inoculated tissues, respectively.

DNA sequence analysis

A single-run DNA sequence analysis was performed on all positive clones identified by Southern analysis. 200–300 bases were analyzed using the GCG program from the University of Wisconsin. The full length of the PAR-1b gene was sequenced by generating nested deletions with the Erase-A-Base system (Promega, Madison, Wis.) according to the manufacturer's protocols. All double-strand DNA deletions were sequenced using the dideoxy chain termination method. The sequencing reaction was performed using a T7 sequencing Kit (USB, Cleveland, Ohio).

RNA extraction and hybridization

Infected leaves were harvested and frozen in liquid nitrogen and stored at $-80°$ C. until RNA extraction. Total RNA was extracted by phenol/chloroform essentially as described by Berry et al. (1985) with some modifications on the extraction buffer (50 mM Tris.HCl, pH8.0, 20 mM EDTA, 100 mM NaCl, and 2% SDS). For RNA blots, 10 µg of total RNA was loaded in each lane. RNA was separated on 1.2% agarose gels containing 18% formaldehyde and transferred to a Nytran Plus membrane (Schleicher and Schuell, Inc., Keene, N.H.). RNA was fixed to the membrane by cross-linking with UV light and then baked at 80° C. for 2 h. Prehybridization and hybridization were performed at 60° C. in 0.5M phosphate buffer (pH 7.2), containing 1% BSA, 7% SDS, and 1 mM EDTA (Church and Gilbert, 1984). The membranes were washed twice in 2×SSC at room temperature for 10 min each, twice in 2×SSC containing 0.5% SDS at 65° C. for 30 min, and twice in 0.1×SSC at room temperature for 30 min each. The probes were prepared from linearized DNA fragments and labeled with $^{32}$p using the random-prime labeling method (Feinberg and Vogelstein, 1984). The PR-1a DNA clone was previously isolated in our lab and the tobacco PAL DNA clone was kindly provided by Michel Legrand and Bernard Fritig, Centre National de la Recherche Scientifique, Strasbourg, France.

SA and SAG assay

SA and its conjugate, SAG, were extracted and analyzed as described by Bowling et al. (1994). Briefly, 1 g of tissue was homogenized and extracted first in 3 ml of 90% and then in 3 ml 100% methanol. The dried residue was resuspended in 2.5 ml of 5% trichloroacetic acid and extracted with 5 ml of ethylacetate-cyclopentane-isopropanol (50:50:1). SA and SAG were separated into the organic and aqueous phases, respectively. The aqueous phase containing the total conjugated SA was boiled for 30 min to release SA, then extracted with organic solvent (ethylacetate-cyclopentane-isopropanol). SA was quantitated by HPLC on an aromatic acid column in 0.01 N $H_2SO_4$.

RESULTS

Isolation of tobacco genes induced early after TMV infection

During the past decade, a large number of genes whose expression is activated by TMV infection of resistant tobacco cultivars have been cloned. However, the techniques and libraries used in these studies favored isolation of genes which are abundantly expressed late (i.e. several days) after infection. Many of these late-expressed genes encode different PR proteins (Dempsey and Klessig, 1995). Other genes involved in plant defenses may have gone undetected because they are transiently expressed at earlier times and/or to lower levels than the "classical" PR genes.

To increase the likelihood of identifying genes expressed early after TMV infection, we took advantage of the reversible, temperature-dependent nature of resistance to TMV in tobacco. When TMV-inoculated plants are maintained at 32° C., HR development is blocked and the population of infected cells continuously increases as the virus replicates and spreads to surrounding cells. Shifting these plants to 22° C. then causes a synchronous activation of the HR in a large population of cells. Since the infection process in tobacco maintained at 22° C. is asynchronous and occurs only in a small number of cells, a cDNA library prepared from temperature-shifted plants should contain an enhanced population of HR-associated clones. Furthermore, by generating our cDNA library from RNA isolated at 4 h post temperature shift, when little to no PR gene expression can be detected (FIG. 1B and Malamy et al., 1992), we were able to significantly reduce the number of otherwise abundant PR clones.

We performed two rounds of differential screening on this library with CDNA probes prepared from tissue isolated from TMV- or mock-inoculated plants maintained at 22° C. From this screen, 17 cDNA clones that were differentially expressed following TMV infection, were identified. Each cDNA insert was initially sequenced at its 5' end and each sequence was compared with the GenBank/EMBO databases. Based on this analysis, these 17 clones were placed into seven groups (Table 1).

TABLE 1

Characteristics of induced cDNA clones

| # of Clones | Size of mRNA[a] | Gene | Reference |
|---|---|---|---|
| 1 | 1,400 | 1-Aminocyclopropane-1-carboxylate oxidase | Knoester et al. 1995 |
| 3 | 1,700 | 1-Aminocyclopropane-1-carboxylate deaminase | Knoester et al.[b] |
| 1 | 2,400 | 3-Hydroxy-3-methylglutaryl-CoA reductase | Genschik et al., 1992 |
| 1 | 1,000 | Ascorbate peroxidase | Orvar and Ellis, 1995 |
| 2 | 1,000 | Chitinase | Payne et al., 1990 |
| 8 | 487–750 | SAR8.2(a, b, d, 1[c],m[c]) | Ward et al., 1991 |
| 1 | 852 | PAR-lb | Herbers et al., 1995 |

[a]Estimated number of nucleotides.
[b]The sequence has been submitted to the EMBL/GenBank/DDBJ databases, but has not yet been published.
[c]New members of the SAR8.2 family; accession numbers for SAR8.21 and SAR8.2m are U96152 and U89604, respectively.

Five of the groups shown in Table I encode well characterized plant enzymes involved in hormone metabolism (ACCO, ACCD), isoprenoid metabolism (HMGR), oxidative stress (APX), or resistance response to pathogen attack (PR-3). The sixth group, consisting of at least five members, corresponds to the SAR8.2 genes, which are associated with SAR. Five members of this family were previously identified (SAR8.2a–e; Alexander et al., 1992); our screen picked up three of these genes and revealed two new members (Table 1). Full-length cDNAs for the two new members were obtained and their entire sequence was determined. These two clones are designated SAR8.21 and SAR8.2 m, based on sequence comparison with other SAR8.2 genes.

The seventh group of clones is homologous to the PAR-1 genes (PAR-1a–c) identified by Herbers et al. (1995). Sequence analysis showed that the aforementioned PAR-1 clone is identical to PAR-1b; it appears to contain a full-length cDNA insert of 852 bp that encodes a 185 amino acid protein with a predicted molecular weight of 21.1 kD. Using this PAR-1b cDNA clone as a probe to screen the library, we obtained eight more cDNA clones whose sequences were identical or highly homologous to PAR-1b. These results suggest that there is little, if any, expression of the other two members of the PAR-1 gene family in tobacco plants resisting TMV infection.

Gene activation is associated with resistance to TMV

To determine whether induction of these seven groups of genes correlated with disease resistance, leaves from the Xanthi nc cultivar, which carries the N resistance gene, or the near isogenic, TMV-susceptible Xanthi cultivar, were harvested at various; times after TMV- or mock-inoculation. Northern analysis (FIG. 1A) indicated that all seven groups were induced in the inoculated leaves by 48 h post inoculation (hpi); induction of most of these genes was evident by 30 hpi (data not shown). Some of these genes also exhibited significant basal levels of expression (e.g. those encoding ACCO, ACCD, and APX). In contrast, none of these genes were induced after TMV inoculation of susceptible Xanthi plants (data not shown) or mock-inoculation of Xanthi nc plants (FIG. 1A) with the exception of APX, whose mRNA levels were elevated after mock-inoculation. As controls, expression of the PR-1 and PAL families of genes were also monitored. PR-1 genes exhibited substantial activation by 48 h after TMV infection of Xanthi nc plants, but were not induced in TMV-inoculated Xanthi plants. The PAL genes showed little to no induction in either Xanthi nc or Xanthi plants after TMV infection (FIG. 1A).

To monitor the activation of these genes more closely, their induction was analyzed in mock- or TMV-inoculated Xanthi nc plants that were maintained at 32° C. for 48 hpi and then shifted to 22° C. for increasing lengths of time to permit HR development (FIG. 1B). At 32° C., when development of resistance is blocked, there was little expression of any of these genes, including the two controls, with the exception of APX which exhibited a moderately high basal level of expression. Within 2 to 4 h of the temperature shift to 22° C., six of the seven groups of genes were activated. Increased expression of APX, however, was not evident until 6 h after the temperature shift. Accumulation of mRNAs for all of these genes reached maximal levels by 6 h, with the exception of the PR-3 (an acidic chitinase) gene whose mRNA levels increased throughout the time course. In contrast to the majority of these seven groups, the PR-1 genes were not activated until 6 h after the temperature shift and their mRNA levels continued to increase throughout the time course. The PAL genes also were not induced until 6 h and their expression was very weak. In sum, these results demonstrate that all seven groups of genes, as well as the PAL and PR-l genes, are induced specifically in resistant tobacco plants after TMV inoculation. However, the activation kinetics for all but one group are different from those of the PR-1 and PAL genes; their mRNA levels are induced more rapidly, and they accumulate to greater extents and reach maximal levels at earlier times after the temperature shift than either PAL or PR-1, respectively.

Activation of the seven groups of genes is independent of SA

The more rapid activation of most of these genes following a temperature shift, compared to that of the PR-1 genes, suggested that their induction might be independent of SA, which is known to be an important endogenous signal for PR gene activation (Klessig and Malamy, 1994; Hammond-Kosack and Jones, 1996; Ryals et al., 1996; Wobbe and Klessig, 1996). Two approaches were used to test this hypothesis. First, the kinetics of SA accumulation after temperature shift (FIG. 2) were compared to the kinetics of mRNA accumulation for all seven groups (FIG. 1B). Second, expression of these genes was monitored in NahG transgenic Xanthi nc tobacco (FIG. 3), in which the SA signal is destroyed by its conversion to catechol (Gaffney et al., 1993).

Large increases in the levels of SA and its conjugated glucoside (SAG) were not detected until 6 and 8 h, respectively, after TMV-infected tobacco were shifted from 32° C. to 22° C. (FIG. 2). Since expression of six of the seven groups was induced by 4 h after temperature shift (FIG. 1B), activation of these genes appears to precede any substantial increase in SA levels. However, modest SA increases of approximately two- to four-fold were detected as early as 2 to 4 h post shift (FIG. 2 insert) and they may have been responsible for activation of these genes. In contrast, the PR-1 genes, whose expression is SA dependent, exhibited little, if any, induction at these early times (FIG. 1B).

Results with the NahG transgenic plants provided additional definitive information. When NahG plants were inoculated with TMV, all of the seven groups were induced with similar kinetics and to similar levels as those observed in wild-type Xanthi nc plants (compare FIGS. 3A to 1A). Similarly, when TMV-inoculated NahG plants were shifted from 32° C. to 22° C., the pattern of mRNA accumulation for these seven groups was almost identical to that detected in wild-type plants (compare FIGS. 3B to 1B). In contrast, PR-1 gene expression was completely blocked in the NahG plants after the temperature shift and only very low levels of PR-1 mRNAs were detected in NahG plants infected under the 22° C. condition (FIG. 3). Interestingly, the induction of PAL gene expression was greater in the TMV-infected NahG plants than that observed in the wild-type plants.

Figure 4:
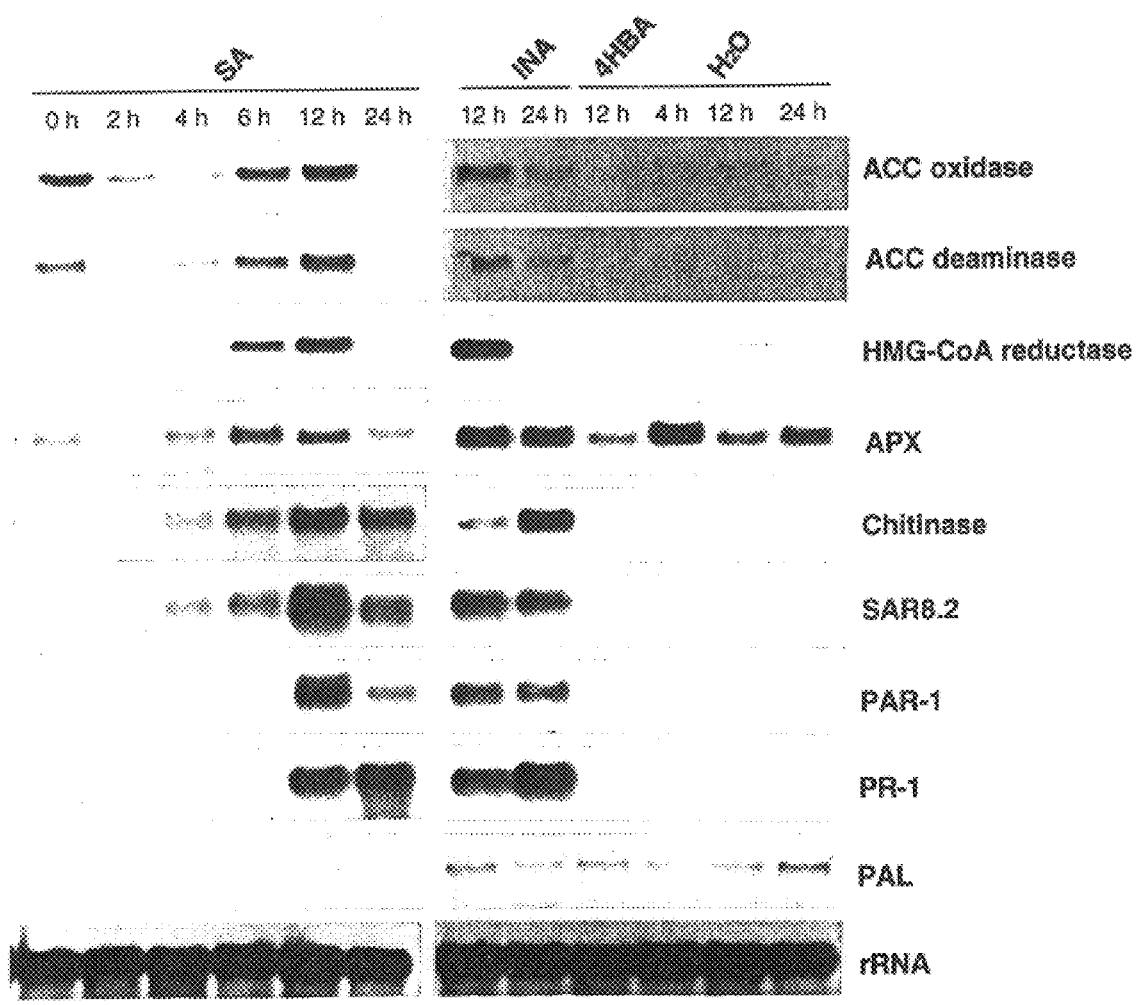
FIG. 4 shows kinetics of gene expression in tobacco plants following treatment with SA, INA and a SA analog. One leaf on each plant was injected with water, 1 mM of SA, INA or 4-hydroxybenzoic acid (4HBA). At the times indicated, injected leaves from two similarly treated plants (~5 g tissue) were harvested and total RNA was extracted. Ten $\mu$g of RNA was loaded in each lane. The experiment with all ten probes was done twice.

Expression of these seven groups of genes in NahG plants, despite the apparent destruction of the SA signal, implies that they are activated through a SA-independent pathway. To ensure that the SA signal was indeed destroyed in TMV-infected NahG plants, the levels of SA and SAG were monitored following a temperature shift. This treatment has previously been shown to produce extremely high levels of SA in wild-type plants (FIG. 2; Malamy et al., 1992). Thus, some of this SA might escape destruction by salicylate hydroxylase in NahG plants. However, no elevation in SA or SAG levels could be detected in the TMV-infected NahG plants (FIG. 2), confirming that activation of these seven groups of genes was independent of SA.
Transient activation of all seven groups of genes by SA Although activation of these genes during a resistance response to TMV infection does not require SA, it is possible that SA still affects their induction. To determine whether they respond to SA and other chemical inducers of PR genes, their expression was monitored in tobacco leaves injected with SA, INA, or 4HBA (a biologically inactive analog that does not: induce PR genes or enhance disease resistance). Within 4 to 6 h after SA injection, six of the seven groups were induced (FIG. 4). In addition, while increased expression of PAR-1 was not detected until 12 h after SA treatment in this experiment, other experiments have demonstrated that it was activated earlier than PR-1 genes (data not shown). By 12 h post treatment, mRNA levels for all of these genes had peaked and by 24 h they had declined. Thus, SA treatment induced their expression transiently, whereas TMV infection caused a sustained elevation in mRNA levels throughout a 72 h time course (FIG. 1A). The elevated expression seen at the 0 h time point for ACCO and ACCD may have been due to a very transient activation caused by injection, as the leaves were harvested 5–10 minutes after injection. In contrast to these results, PR-1 mRNAs were not readily detected until 12 h post treatment and they continued to increase through 24 h. There was little, if any, induction of PAL. These seven families were also induced by INA, generally in a transient manner (FIG. 4). On the other hand, the inactive analog 4HBA failed to activate these genes. Thus, we conclude that SA and its functional analog INA, but not a biologically inactive analog 4HBA, can transiently activate these seven groups of genes.
All seven groups of genes exhibit systemic induction To determine whether expression of these genes was associated with SAR, their respective mRNA levels were determined in the upper uninoculated leaves of TMV-resistant Xanthi nc plants at various times after inoculation of the lower leaves (FIG. 5A). All seven groups of genes were activated in the uninoculated leaves by six days post inoculation (dpi), with some exhibiting low levels of induction by 3 dpi. The PR-1 genes were also systemically induced by 6 dpi, as expected, and the PAL genes exhibited a low level of systemic induction (FIG. 5A). Taken together, these results indicate that activation of these seven groups of genes is associated with SAR, as well as local resistance at and surrounding the site of infection.

A similar experiment was performed using NahG plants to determine whether expression of these genes could be systemically activated in the absence of increases in endogenous SA (FIG. 5B). Based on whether their expression was altered in the systemic leaves of NahG vs wild-type plants, these seven groups of genes could be divided into two categories. Three genes, ACCO, ACCD and APX, exhibited similar levels of induction in the uninoculated leaves of both wild-type and NahG plants (FIG. 5B). While induction may have been slightly delayed in NahG plants, its level of expression was equal to or greater than that seen in wild-type plants. Thus, their systemic expression appears to be SA independent. In contrast, the induction of the other four groups of genes, HMGR, PR-3, SAR8.2 and PAR-1, was delayed and markedly reduced in the uninfected leaves of NahG plants (FIG. 5B). Thus, efficient systemic expression of these genes appears to be somewhat SA dependent, although their expression in the TMV-infected leaves is SA independent. In fact, to compare the expression of these genes in NahG and wild-type plants, the autoradiograms from the NahG plants had to be exposed five times longer than those from wild-type plants. Overall, the levels of induction for these genes were 5–20 fold lower in the systemic leaves of NahG plants than those observed in wild-type plants. Expression of SA-dependent PR-1 genes was not detected in the uninoculated leaves of NahG plants, even after an 18-fold longer exposure than that used for wild-type plants. It is notable that the PAL genes were more strongly induced in NahG plants than in wild-type plants.

In sum, our results indicate that these seven groups of genes are induced in the uninfected, systemic leaves through either a totally or a partially SA-independent pathway. This finding, in combination with the SA-independent expression of these genes in TMV-inoculated leaves and different expression kinetics of these genes, differentiates them from other defense-related genes. Thus, we have designated this set SIS genes, for SA-independent, systemically induced.

EXAMPLE 2

Isolation and Characterization of a Tobacco Epoxide Hydrolase Induced During the Resistance Response Epoxide hydrolase (EH; EC 3.3.2.3) catalyzes the conversion of endogenous and exogenous epoxides to diols by the addition of water (Oesch, 1973). In mammals, several groups of EHs have been characterized based on their enzymatic activity and cellular location.

Little is known about the actual function of EHs in plants, although they appear to be involved in the biosynthesis of cutin (Pinot et al., 199:2). Cutin is a structural component of the cuticle, which among other functions can serve as a physical barrier to prevent pathogen attack (Kolattukudy, 1980, 1981, 1984). One role of EHs may be to reinforce or restore the cuticle which can be damaged during infection. Currently, a fatty acid EH has been characterized from soybean and several soluble EH (sEH) genes have been identified in Arabidopsis and potato (Blée and Schuber, 1992; Stapleton et al., 1994; Kiyosue et al., 1994). Transcripts for the soluble potato EH genes have been shown to accumulate after wounding or treatment with exogenous methyl jasmonate (Stapleton et al., 1994), while AtsEH, the sEH gene from Arabidopsis, was induced by drought stress or auxin treatment (Kiyosue et al., 1994). Based on these limited data, plant EHs appear to play a role in responding to environmental stresses.

In addition to its participation in cutin biosynthesis, EH may have another role during plant defense responses. In several plant-pathogen interactions, including infection of tobacco by TMV (Doke and Ohashi, 1988), the HR is preceded by the rapid production and accumulation of reactive oxygen species (ROS; Mehdy, 1994; Baker and Orlandi, 1995; Hammond-Kosack and Jones, 1996; Low and Merida, 1996). Hydrogen peroxide and superoxide anion are the two major ROS, which are produced during this oxidative burst. They may act directly as antimicrobial agents and may serve as second messengers or signals to facilitate activation of some of the defense genes at the site of infection. They may also play a role in initiating the HR (Levine et al., 1994; Auh and Murphy, 1995; Jabs et al., 1996). However, the ROS can also have deleterious effects on the host. For example, the highly reactive and destructive hydroxyl radical, which can be formed from superoxide anion and hydrogen peroxide via the Fenton or Haber-Weiss reactions, can damage a diverse array of biological molecules including the generation of epoxides from unsaturated hydrocarbons.

As discussed above, SA plays a key role in the activation of a subset of the defense genes, including the PR genes (Linthorst, 1991; Cutt and KLessig, 1992), and is required for SAR establishment in the tobacco-TMV system, as well as in other plant-pathogen interactions in Arabidopsis, cucumber and potato (Malarny et al., 1990; Gaffney et al., 1993; Durner et al., 1997; Yang et al., 1997). However, several other defense genes are induced through a SA-independent signaling pathway(s) (See Example 1; and Penninckx et al., 1996; Pieterse et al., 1996; Vidal et al., 1997). In this Example we report the isolation of a tobacco EH gene, termed EH-1, which is induced locally and systemically by TMV infection. This gene appears to be induced via a SA-independent pathway since it can be activated by TMV infection in SA-deficient NahG plants. However, differences between the induction kinetics of EH-1 in wild-type and NahG plants, suggested that this pathway can be influenced by SA. EH-1 is the first plant EH gene whose expression is associated with disease resistance.

EXPERIMENTAL PROCEDURES
Plant material and inoculation
Plant materials and inoculation procedures were as described in Example 1.
Chemical Treatments
2,4-D, Sik, and its analog 4HBA were purchased from Sigma. IAA was purchased from GIBCO BRL. INA was provided by Uwe Conrath at Universitat Kaiserslautern, Germany. SA, 4HBA and INA were dissolved in water and adjusted to Et pH of 6.5. They were injected into plants at a concentration of 1 mM with a needle-less syringe. Control plants were injected with distilled water. IAA and 2,4-D was dissolved in 0.2% ethanol.

Cell suspension was treated with auxins as described by Xiang et al (1996). Cell cultures were grown in hormone-free medium for 2 days to deplete hormones in the medium. IAA (100 $\mu$M) and 2,4-D (100 $\mu$M) were added to the suspension. Cells were harvested at 0, 2, 6 and 12 h after addition of auxins. Water was added to the control.
Isolation of cDNA of EH-1 and DN4A Sequencing
The EH-1 gene was isolated by screening a TMV-induced cDNA library by differential screening as described in Example 1. Probes were prepared from 1 $\mu$g of mRNA extracted from tobacco leaves harvested at 48 h after TMV or mock treatment and labeled with alpha-$^{32}$-P (Sambrook et al., 1989). After two rounds of screening, the positive clone was excised from the vector according to the instructions of manufacturer (Stratagene). Nucleotide sequence of EH-1 was determined on both strands with the dideoxy chain termination method. The sequencing reaction was performed using T7 sequencing kit (Pharmacia). The results were analyzed using the LASERGENE (DNASTAR, Inc.) and GCG program (University of Wisconsin).
Northern and Southern Analyses
Total RNA was isolated from tobacco tissue by phenol/chloroform as described in Example 1. Ten micrograms of total RNA was analyzed by electrophoresis in a 1.2% agarose gel containing formaldehyde and blotted to Nytran Plus membranes (Schleicher and Schuell). Blots were hybridized with [alpha-$^{32}$P]dCTP-labeled probes prepared by the random-priming method with a oligo labelling kit (Pharmacia). Total genomic DNA was extracted from tobacco plants according to the method described by Das et al. (1990). DNA (10 $\mu$g) was digested with restriction enzymes and resolved by electrophoresis on a 0.7% agarose gel. The DNA was transferred to a Nytran Plus membrane. Following autoradiography, mRNA levels were quantitated using a Phosphorimager (Molecular Dynamics).

RESULTS
Cloning and Analysis of an epoxide hydrolase cDNA
In order to identify novel TMV-induced defense genes, a cDNA library was constructed with mRNA prepared from TMV-infected tobacco leaves, as described in Example 1. Differential screening of this library with probes generated from mock- and TMV-inoculated tobacco leaves identified a variety of TMV-induced clones (Example 1). Sequence analysis indicated that one clone shared homology with the sEH genes previously isolated from potato and Arabidopsis (Kiyosue et al., 1994; Stapleton et al., 1994).

The tobacco sEH cDNA clone contained a unique sequence at the 5' end of the open reading frame that might represent an unspliced intron. To determine whether other sEH cDNAs contained this sequence, the TMV-induced tobacco cDNA library was rescreened using the original EH clone as a probe. After primary screening, the candidate clones were examined by PCR using two specific primers corresponding to the regions upstream and downstream of the putative EH intron. Nine of 11 samples represented completely spliced clones, suggesting that the original CDNA was generated from an incompletely spliced transcript. One of the nine cDNA clones corresponding to the fully spliced mRNA was designated EH-1 and analyzed further. This clone contains an insert of 1238 bp and encodes a protein of 312 amino acids with a predicted molecular weight of 35.4 kD (FIG. 6).

Figure 7:
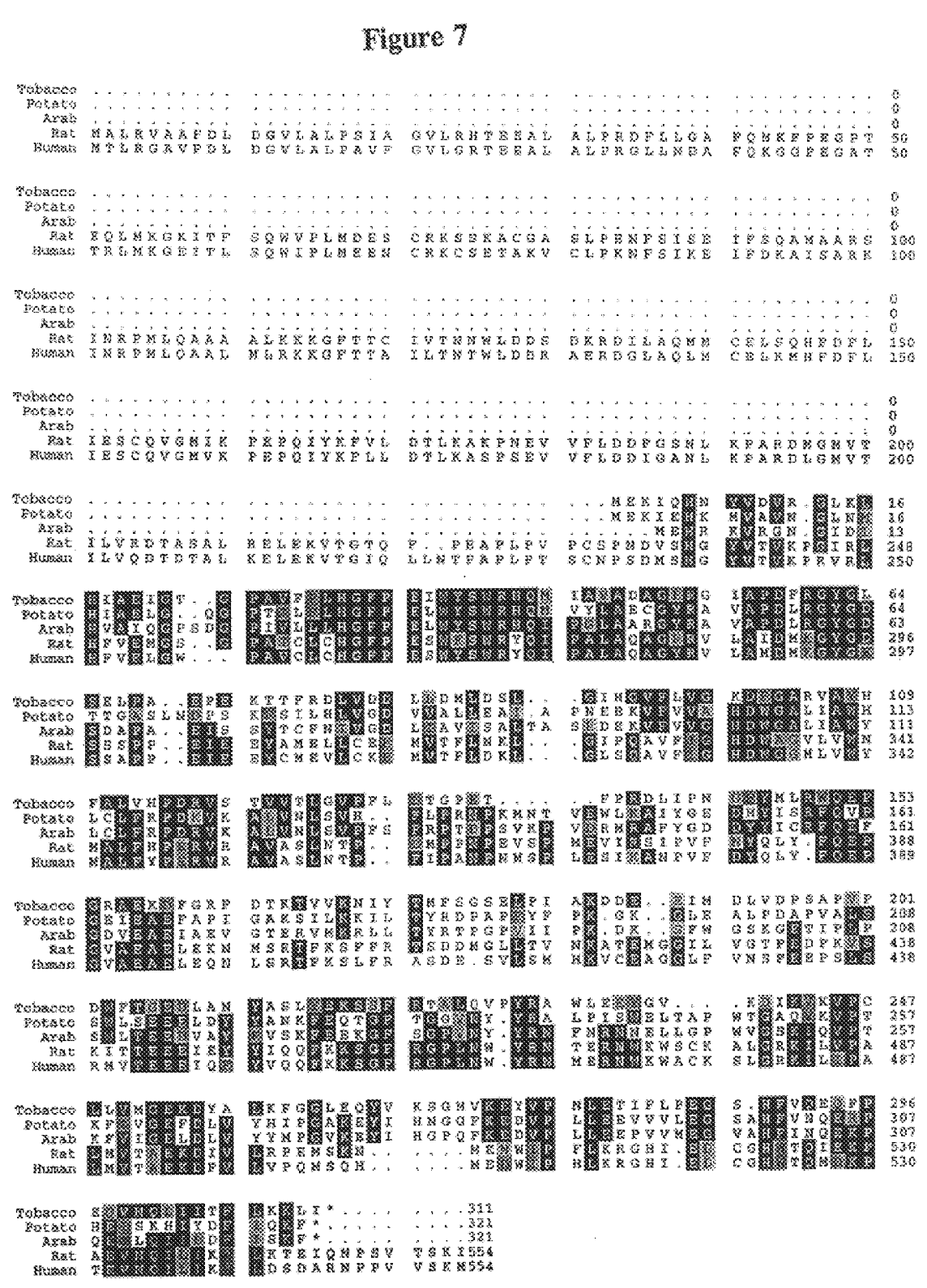

The sequence of EH-1 shows homology to EHs from both plants and mammals (FIG. 7). The amino acid sequence of EH-1 possesses 37% identity and 64% similarity to the potato and Arabidopsis sEHs. Slightly less identity and similarity were found with human and rat sEHs (33–35%, 58–60%, respectively). At the CDNA level, the percent identities between EH-1 and potato, Arabidopsis, rat and human sEH's were 49%, 48%, 45% and 42%, respectively (data not shown). Like potato and Arabidopsis sEHs, tobacco EH-1 does not contain the N-terminal third of mammalian sEHs. Since both the recombinant potato and Arabidopsis sEH proteins produced in *E. coli* exhibit functional EH activity (Kiyosue et al., 1994; Stapleton et al., 1994), EH-1. is believed to encode a full length, functional protein.

Figure 8:
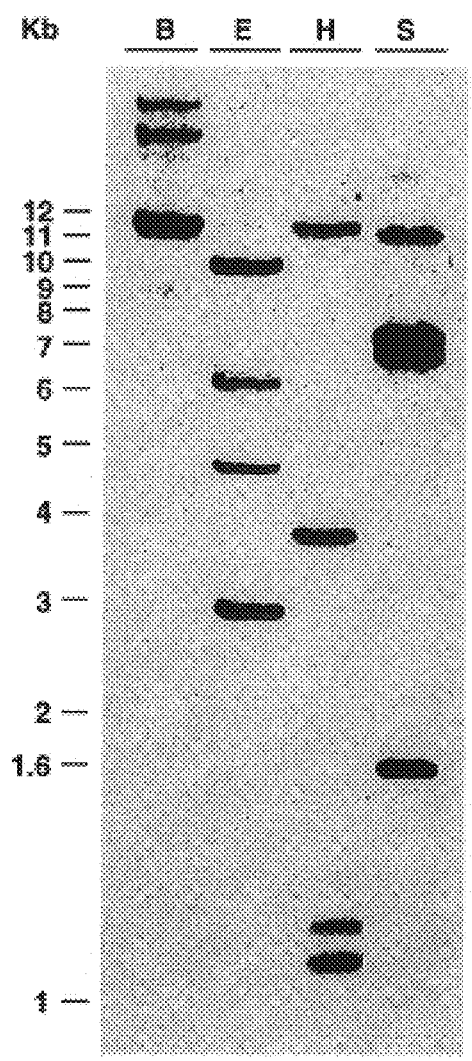
FIG. 8 shows a Southern blot analysis of tobacco DNA with EH-1 clone as a probe. After digestion with BamHI (B), EcoRI (E),HindIII (H) and ScaI (S), ten $\mu$g of tobacco genomic DNA was loaded in each lane. After electrophoresis and transfer, the blot was hybridized with the labeled EH-1 clone.

Genomic DNA was isolated, digested with BamHI, EcoRI, HindIII and Sca I and hybridized with the full length EH-1 clone. One or two strongly hybridizing bands and a few weaker bands were observed with each digestion (FIG. 8). Based on these results, EH appears to be encoded by a very small gene family in tobacco. However, since tobacco (Nicotiana tabacum) is amphidiploid, these different bands could represent identical EH genes derived from the two parental genomes or they could represent different EH genes.

Activation of EH-1 expression by TMV infection is associated with resistance. To examine whether EH-1 expression correlates with disease resistance, mRNA was isolated from the inoculated leaves of both resistant (Xanthi nc) and susceptible (Xanthi) plants at various times after inoculation with TMV. Increases in EH-1 transcripts were detected by 30 h post inoculation (hpi) in resistant plants maintained at ambient: temperature (22° C.); their levels peaked at 48 hpi (FIGS. 9A, 9B). In contrast, no induction of EH-1 expression was observed in the susceptible plants (data not shown) or in the mock-inoculated control plants (FIGS. 9A, 9B). Expression of the resistance- associated PR-1 genes was also monitored. Unlike EH-1, transcripts for the PR-1 genes were first readily detected at 36 hpi, and continued to increase throughout the time course.

Interestingly, EH-1 was induced to similar levels in the TMV-inoculated leaves of transgenic NahG tobacco plants, which are unable to accumulate SA due to the synthesis of salicylate hydroxylase (Gaffney et al., 1993). However, the induction of the EH-1 gene was delayed, occurring 6 h later in NahG plants than in wild-type plants (FIGS. 9C, 9D). By contrast, PR-1 gene expression, which is SA dependent, was severely suppressed in NahG plants. Thus, EH-1 activation after TMV infection appears to be mediated, at least in part, by a SA-independent pathway.

Activation of EH-1 expression by TMV infection after a temperature shift

At high temperatures (above 28° C.), resistance to TMV is blocked and tobacco plants become systemically infected (Kassanis, 1952; Gianinazzi, 1970). Furthermore, these plants fail to develop a HR, accumulate SA or express PR genes (Yalpani et al., 1991; Malamy et al., 1992). When they are shifted to lower temperatures, resistance to TMV is restored and a rapid and dramatic increase in SA levels precedes both PR gene expression and the appearance of a HR (Malamy et al., 1992).

The TMV-infected plants maintained at 32° C. for 48 h, exhibited only basal levels of EH-1 gene expression. After these plants were transferred to 22° C., EH-1 transcripts accumulated rapidly (FIGS. 10A, 10B). This induction was observed by 2 h after the temperature shift and mRNA levels increased steadily throughout the time course. In contrast, transcripts for the PR-1 genes were not detected until 8 h post temperature shift. Neither EH-1 nor PR-1 were induced in the temperature-shifted, mock-inoculated plants.

In the temperature-shifted NahC plants, EH-1 induction kinetics were similar to those observed in wild-type plants (FIGS. 10C, 10D). At 2 h after temperature shift, expression of EH-1 was slightly higher in wild-type plants than that in NahG plants. However, the level of EH-1 mRNA in the NahG plants at 8 h post temperature shift was 2-fold higher than that detected in wild-type plants (maximum of wild-type plants vs maximum of NahG plants). Therefore, expression levels of EH-1 overall were stronger in NahG plants than those in wild-type plants (FIG. 10). As expected, little or no PR-1 gene expression was detected in the TMV-infected, temperature-shifted NahG plants.

In these temperature-shift experiments, activation of EH-1 gene expression preceded both accumulation of SA and induction of PR-1 genes. Substantial increases in SA levels were not detected until 6 h after shifting infected wild-type plants from 32° C. to 22° C. (see Example 1; FIG. 2). Furthermore, no accumulation of SA could be detected in infected NahG plants shifted to 22° C. Therefore, the rapid induction of the EH-1 gene in TMV-infected wild-type and NahG plants after the temperature shift suggested that activation of this gene is associated with resistance but independent of SA.

Systemic induction of the EH-1 gene

In order to determine whether EH-1 is systemically induced after TMV infection, mRNAs were isolated and analyzed from upper uninoculated leaves. An increase in EH-1 transcript levels were first observed at 3 days post inoculation (dpi) in the systemic leaves. While they peaked by 6 dpi, they remained elevated throughout the duration of the time course (FIGS. 11A, 11B). Induction of EH-1 expression was also detected in the uninoculated leaves of TMV-infected NahG plants; however, it was delayed and 5 fold weaker compared to that observed in wild-type plants (FIGS. 1C, 1D). Thus, EH-1 expression in the systemic leaves can be induced via a SA-independent pathway, although SA was required for full gene induction.

Rapid and substantial activation of EH-1 expression by SA and INA, but not by auxin The kinetics of EH-1 gene expression following treatment with SA, INA (a functional analog of SA) or 4HBA (a biologically inactive SA analog) were also examined. Within 2 h after SA injection, the level of EH-1 transcripts had increased over background (FIGS. 12A, 12B). By 6 h post treatment it reached a peak and the levels then decreased throughout the remainder of the time course. Treatment with INA also induced a transient accumulation of EH-1 transcripts. In contrast, injection of 4HBA failed to induce a detectable increase EH-1 expression. Transcripts for the PR-1 genes were also monitored after SA treatment and their expression kinetics were substantially different than those for EH-1. PR-1 transcripts were first detected at 12 h post treatment and they continued to increase throughout the time course.

An Arabidopsis sEH gene was previously shown to be induced by auxins including 2,4-dichlorophenoxy acetic acid (2,4-D), naphthalene acetic acid and indole-3-acetic acid (IAA) (Kiyosue et al., 1994). To investigate if EH-1 was induced by auxins, tobacco suspension cells were grown in hormone-free medium for 2 days to deplete any residual hormones in the media and then treated with either 2,4-D or IAA. EH-1 expression was then monitored at various times after the addition of auxin. Little or no induction was detected after treatment with 2,4-D and IAA (FIG. 12C). As a positive control for auxin treatment, expression of an auxin-inducible glutathione S-transferase gene, GNT35, from tobacco was monitored. In contrast to EH-1, GNT35 was rapidly induced by both 2,4-D and IAA treatments (FIG. 12C).

REFERENCES

Alexander, D., Stinson, J., Pear, J., Glascock, C., Ward, E., Goodman, R. M. and Ryals, J. (1992) A new multigene family inducible by tobacco mosaic virus or salicylic acid in tobacco. Mol. Plant-Microbe Interact. 5, 513–515.

Auh, C.-K., and Murphy, T. M. (1995) Plasma membrane redox enzyme is involved in the synthesis of $O_2^-$ and $H_2O_2$ by phytophthora elicitor-stimulated rose cells. Plant Physiol. 107, 1241–1247.

Baker, C. J. and Orlandi, E. W. (1995) Active oxygen in plant pathogenesis. Annu. Rev. Phytopathol. 33, 299–321.

Beetham, J. K., Grant, D., Arand, M., Garbarino, T. K., Pinot, F., Oesch, F., Belknap, W. R., Shinozaki, K. and Hammock, B. D. (1995) Gene evolution of epoxide hydrolases and recommended nomenclature. DNA Cell Biol. 14, 61–71.

Beetham, J. K., Tian, T. and Hammock, B. D. (1993) cDNA cloning and expression of a soluble epoxide hydrolase from human liver. Arch. Biocheni. Biophys. 305, 197–201.

Berry, J. O., Nikolau, B. J., Carr, J. P. and Klessig, D. F. (1985) Transcriptional and post-transcriptional regulation of ribulose 1,5-bisphosphate carboxylase gene expression in light-and dark-grown Amaranth cotyledons. Mol. Cell Biol. 5, 2238–2246.

Blée E. and Schuber, F. (1990) Effecient epoxidation of unsaturated fatty acids by a hydroperoxide-dependent oxygenase. J. Biol. Chem. 265, 12887–12894.

Blée E. and Schuber, F. (1992) Occurrence of fatty acid epoxide hydrolases in soybean (Glycine max.) Biochem. J. 267, 11881–11887.

Blée E. and Schuber, F. (1993) Biosynthesis of cutin monomers: involvement of alipoxygenase/peroxygenase pathway. Plant J. 4, 113–123.

Boller, T. (1991) Ethylene in pathogenesis and disease resistance. In The Plant Hormone Ethylene (Mattoo, A. K. and Suttle, J. C. eds). Boca Raton: CRC Press, pp. 293–314.

Boller, T., Gehri, A., Mauch, F. and Vbgeli, U. (1983) Chitinase in bean leaves: induction by ethylene, purification, properties, and possible function. Planta 157, 22–31.

Bowles, D. J. (1990) Defense-related proteins in higher plants. Annu. Rev. Biochem. 59, 873–907. Bowling, S. A., Guo, A., Cao, H., Gordon, A. S., Klessig, D. F. and Dong, X. (1994) A mutation in Arabidopsis that leads to constitutive expression of systemic acquired resistance. Plant Cell 6, 1845–1857.

Cao, H., Bowling, S. A., Gordon, A. S. and Dong, X. (1994) Characterization of an Arabidopsis mutant that is nonresponsive to inducers of systemic acquired resistance. Plant Cell 6, 1583–1592.

Chappell, J. (1995) The biochemistry and molecular biology of isoprenoid metabolism. Plant Physiol. 107, 1–6.

Chivasa, S., Murphy, A. M., Naylor, M. and Carr, J. P. (1997) Salicylic acid interferes with tobacco mosaic virus replication via a novel salicylhydroxamic acid-sensitive mechanism. Plant Cell 9, 547–557.

Church, G. M. and Gilbert, W. (1984) Genomic sequencing. Proc. Natl. Acad. Sci. USA 8L, 1991–1995.

Conklin, P. L. and Last, R. L. (1995) Differential accumulation of antioxidant mRNAs in Arabidopsis thaliana exposed to ozone. Plant Physiol. 109, 203–212.

Conrath, U., Chen, Z., Ricigliano, J. and Klessig, D. F. (1995) Two inducers of plant defense responses, 2,6-dichloroisonicotinic acid and salicylic acid, inhibit catalase activity in tobacco. Proc. Natl. Acad. Sci. USA 92, 7143–7147.

Cutt, J. R. and Klessig, D. F. (1992) Pathogenesis- related proteins. In Plant Gene Research, Genes Involved in Plant Defense (Meins, F. and Boller, T., eds.). New York: Springer-Verlag, pp. 209–243.

Das, O. P., Alvarez, C., Chaudhuri, S. and Messing, J. (1990) Molecular methods for genetic-analysis of maize. Methods Mol. Cell. Biol. 1, 213–222.

Delaney, T. P., Friedrich, L. and Ryals, J. (1995) Arabidopsis signal transduction mutant defective in chemically and biologically induced disease resistance. Proc. Natl. Acad. Sci. USA. 92, 6602–6606.

Delaney, T., Uknes, S., Vernooij, B., Friedrich, L., Weymann, K., Negrotto, D., Gaffney, T., Gut-Rella, M., Kessmann, H., Ward, E. and Ryals, J. (1994) A central role of salicylic acid in plant disease resistance. Science 266, 1247–1250.

Dempsey, D. A. and Klessig, D. F. (1995) Signals in plant disease resistance. Bull. Inst. Pasteur 93, 167–186.

Dempsey, D. A., Pathirana, M. S., Wobbe, K. K. and Klessig, D. F. (1997) Identification of an Arabidopsis locus required for resistance to turnip crinkle virus. Plant J. 11, 301–311.

De Tullio, M. and Arrigoni, O. (1992) Ascorbate peroxidase activity in resistant and susceptible plants of Lycopersicon esculentum. Boll. Soc. Ital. Biol. Sper. 68, 613–617.

Dietrich, R. A., Delaney, T. P., Uknes, S. J., Ward, E. R., Ryals, J. A. and Dangl, J. L. (1994) Arabidopsis mutants simulating disease response. Cell 77, 565–577.

Dixon, R. A. and Lamb, C. J. (1990) Molecular communication in interactions between plants and microbial pathogens. Annu. Rev. Plant Physiol. Plant Mol. Biol. 41, 339–367.

Doke, N. and Ohashi, Y. (1988; Involvement of an $O_2$—generating system in the induction of necrotic lesions on tobacco leaves infected with tobacco mosaic virus. Physiol. Mol. Plant Pathol. 32, 163–175.

Durner, J., Shah, J. and Klessig, D. F. (1997) Salicylic acid and induction of defense genes. Trends in Plant Sci. 2, 266–274.

Durner, J. and Klessig, D. F. (1995) Inhibition of ascorbate peroxidase by salicylic acid and 2,6-dichloroisonicotinic acid, two inducers of plant defense responses. Proc. Natl. Acad. Sci. USA 92, 11312–11316.

Farmer, E. E. and Ryan, C. A. (1992) Octadecanoid-derived signals in plants. Trends Cell Biol. 2, 236–241.

Feinberg, A. P. and Vogelstein, 13. (1984) A technique for radiolabeling DNA restriction endonuclease fragments to high specific activity. Anal. Biochem. 137, 266–267.

Gaffney, T., Friedrich, L., Vernooij, B., Negrotto, D., Nye, G., Uknes, S., Ward, E., Kessman, H. and Ryals, J. (1993) Requirement of salicylic acid for the induction of systemic acquired resistance. Science 261, 754–756.

Genschik, P., Criqui, M., Parmentier, Y., Marbach, J., Druu, A., Fleck J. and Jamet, E. (1992) Isolation and characterization of a cDNA encoding a 3-hydroxy-3-methylglutaryl coenzyme A reductase from Nicotiana sylvestris. Plant Mol. Biol. 20, 337–341.

Gianinazzi, S. (1970) Hypersensibilite aux virus, temperatures et proteines solubles chez le Nicotiana tabacum cv. Xanthi-nc. C. R. Acad. Sci. Paris D 270, 2382–2386.

Glazebrook, J., Rogers, E. E. and Ausubel, F. M. (1996) Isolation of Arabidopsis mutants with enhanced disease susceptibility by direct screening. Genetics 143, 973–982.

Grant, D. F., Storms, D. H. and Hammock, B. D. (1993) Molecular cloning and expression of murine liver soluble epoxide hydrolase. J. Cell Biol. 108, 1657–1664.

Greenberg, J. T., Guo, A., Klessig, D. F. and Ausubel, F. M. (1994) Programmed cell death in plants: a pathogen-triggered response activated coordinately with multiple defense functions. Cell 77, 551–563.

Hahlbrock K. and Scheel, H. (1989) Physiology and molecular biology of phenylpropanoid metabolism. Annu. Rev. Plant Physiol. Plant Mol. Biol. 40, 347–369.

Hamberg, M. and Gardner, H. W. (1992) Oxylipin pathway to jasmonates: biochemistry and biological significance. Biochim. Biophys. Acta. 1165, 1–18.

Hamberg, M. and Hamberg, G. (1990) Hydroperoxide-dependent epoxidation of unsaturated fatty acids in the broad bean (Vicia faba L.). Arch Biochem. Biophys. 283, 409–416.

Hammond-Kosack, K. E. and Jones, J. D. G. (1996) Resistance gene-dependent plant defense responses. Plant Cell 8, 1773–1791.

Herbers, K., Monke, G., Badur, R. and Sonnewald, U. (1995) A simplified procedure for the subtractive CDNA cloning of photoassimilate-responding genes: Isolation of cDNAs encoding a new class of pathogenesis-related proteins. Plant Mol. Biol. 29, 1027–1038.

Herbers, K., Meuwly, P., Metraux, J.-P. and Sonnewald, U. (1996) Salicylic acid-independent induction of pathogenesis-related protein transcripts by sugars is dependent on leaf developmental stage. FEBS Letts. 397, 239–244.

Honma, M. and Shimomura, T. (1978) Metabolism of 1-aminocyclopropane-l-carboxylic acid. Agric. Biol. Chem. 42, 1825–1831.

Jabs, T., Dietrich, R. A. and Dangl, J. L. (1996) Initiation of runaway cell death in an Arabidopsis mutant by extracellular superoxide. Science 273, 1853–1856.

Kassanis, B. (1952) Some effects of high temperature on the susceptibility of plants to infection with viruses. Ann. Appl. Biol. 39, 358–369.

Kiyosue, T., Beetham, J. K., Pinot, F., Hammock, B. D., Yamaguchi-Shinozaki, K. and Shinozaki, K. (1994) Characterization of an Arabidopsis CDNA for a soluble epoxide hydrolase gene that is inducible by auxin and water stress. Plant J. 6, 259–269.

Klessig, D. F., Durner, J., Chen, Z., Anderson, M., Conrath, U., Du, H., Guo, A., Liu, Y., Shah, J., Silva, H., Takahashi, H. and Yang, Y. (1996) Studies of the salicylic acid signal transduction pathway. In Advances in Molecular Genetics of Plant-Microbe Interactions (Stacey, G., Mullin, B. and Gresshoff, P. M., eds.). The Netherlands: Kluwer Academic Publishers, pp. 33–38.

Klessig, D. F. and Malamy, J. (S1994) The salicylic acid signal in plants. Plant Mol. Biol. 26, 1439–1458.

Knehr, M., Arand, M., Gehel, T., Zeller, H-D., Thomas, H. and Oesch, F. (1993) Isolation and characterization of a cDNA encoding rat liver cytosolic epoxide hydrolase and its functional expression in *Escherichia coli*. J. Biol. Chem. 268, 17623–17627.

Knoester, M., Bol, J. F., van Loon, L. C. and Linthorst, J. M. (1995) Virus-induced gene expression for enzymes of ethylene biosynthesis in hypersensitively reacting tobacco. Mol. Plant-Microbe Interact. 8, 177–180.

Kolattukudy, P. E. (1980) Biopolyester membranes of plants: cutin and suberin. Science 208, 990–1000.

Kolattukudy, P. E. (1981) Structure, biosynthesis, and biodegradation of cutin and suberin. Ann. Rev. Plant Physiol. 32, 539–567.

Kolattukudy, P. E. (1984) Biochemistry and function of cutin and suberin. Can. J. Bot. 62, 2918–2933.

Kolattukudy, P. E. (1985) Enzymatic penetration of the plant cuticle by fungal pathogens. Ann. Rev. of Phytopathol. 23, 223–250.

Lawton, K. A., Potter, S. L., Uknes, S. and Ryals, J. (1994) Acquired resistance signal transduction in Arabidopsis is ethylene independent. Plant Cell 6, 581–588.

Levine, A., Tenhaken, R., Dixon, R. and Lamb, c. (1994) $H_2O_2$ from the oxidative burst orchestrates the plant hypersensitive disease resistance response. Cell 79, 583–593.

Low, P. S. and Merida, J. R. (1996) The oxidative burst in plant defense: Function and signal transduction. Physiol. Plant 96, 533–542.

Linthorst, H. J. M. (1991) Pathogenesis-related proteins of plants. Crit. Rev. Plant Sci. 10, 123–150.

Malamy, J., Carr, J. P., Klessig, D. F. and Raskin, I. (1990) Salicylic acid: a likely endogenous signal in the resistance response of tobacco to tobacco mosaic virus. Science 250, 1002–1004.

Malamy, J., Hennig, J. and Klessig, D. F. (1992) Temperature-dependent induction of salicyhic acid and its conjugates during the resistance response to tobacco mosaic virus infection. Plant Cell 4, 359–366.

Malamy, J., Sanchez-Casas, P., Hennig, J., Guo, A. and Klessig, D. F. (1996) Dissection of the salicylic acid signaling pathway in tobacco. Mol. Plant-Microbe Interact. 9, 474–482.

Mehdy, M. C. (1994) Active oxygen species in plant defense against pathogens. Plant Physiol. 105, 467–472.

Oesch, F. (1973) Mammalian epoxide hydrolases: Inducible enzymes catalyzing the inactivation of carcinogenic and cytotoxic metabolites derived from aromatic and olefinic compounds. Xenobiotica 3, 305–340.

Orvar, B. L. and Ellis, B. E. (1095) Isolation of a cDNA encoding cytosolic ascorbate peroxidase in tobacco. Plant Physiol. 108, 839–840.

Payne, G., Ahl, P., Moyer, M., Harper, A., Beck, J., Meins, F. Jr. and Ryals, J. (1990) Isolation of complementary DNA clones encoding pathogenesis-related proteins P and Q, two acidic chitinases from tobacco. Proc. Natl. Acad. Sci. USA 87, 98–102.

Pellegrini, L., Rohfritsch, O., Fritig, B. and Legrand, M. (1994) Phenylalanine ammonia-lyase in tobacco: Molecular cloning and gene expression during the hypersensitive reaction to tobacco mosaic virus and the response to a fungal elicitor. Plant Physiol. 106, 877–886.

Penninckx, I. A. M. A., Eggermont, K., Terras, F. R. G., Thomma, B. P. H. J., De Samblanx, G. W., Buchala, A., Metraux, J.-P., Manners, J. M. and Broekaert, W. F. (1996) Pathogen-induced systemic activation of a plant defensin gene in Arabidopsis follows a salicylic acid-independent pathway. Plant Cell 8, 2309–2323.

Pieterse, C. M. J., van Wees, S. C. M., Hoffland, E., van Pelt, J. A. and van Loon, L. C. (1996) Systemic resistance in Arabidopsis induced by biocontrol bacteria is independent of salicylic acid accumulation and pathogenesis-related gene expression. Plant Cell 8, 1225–1237.

Pinot, F., Salaun, J.-P., Bosch, H., Lesot, A., Mioskowski, C. and Durst, F. (1992) ω-hydroxylation of Z9-octadecenoic, Z9,10-epoxystearic and 9,10-dihydroxystearic acids by microsomal cytochrome P450 systems from Vicia sativa. Biochem. Biophys. Res. Commun. 184, 183–193.

Rasmussen, J. B., Hammerschmidt, R. and Zook, M. N. (1991) Systemic induction of salicylic acid accumulation in cucumber after inoculation with Pseudomonas syringae pv syringae. Plant Physiolol. 97, 1342–1347.

Reinbothe, S., Mollenhauer, B. and Reinbothe, C. (1994) JIPs and RIPs: the regulation of plant gene expression by jasmonates in response to environmental cues and pathogens. Plant Cell 6, 1197–1209.

Ross, A. F. (1961a) Localized acquired resistance to plant virus infection in hypersensitive hosts. Virology 14, 329–339.

Ross, A. F. (1961b) Systemic acquired resistance induced by localized virus infections in plants. Virology 14, 340–358.

Ryals, J. A., Neuenschwander, U. H., Willits, M. G., Molina, A., Steiner, H.-Y. and Hunt, M. D. (1996) Systemic acquired resistance. Plant Cell 8, 1809–1819.

Ryals, J., Uknes, S. and Ward, E. (1994) Systemic acquired resistance. Plant Physiol. 104, 1109–1112.

Sambrook, J., Fritsch, E. F. and Maniatis, T. A. (1989) Molecular Cloning: A Laboratory Manual. 2nd edition. Cold Spring Harbor Laboratory, Cold Spring Harbor, N.Y.

Schweizer, P., Jeanguénat, A., Mösinger, E. and Metraux, J.-P. (1994) Plant protection boy free cutin monomers in two cereal pathosystems. In Advances in Molecular Genetics of Plant-Microbe Interactions (Daniels, M. J., Downie, J. A. and Osbourn, A. E., eds). Dordrecht: Kluwer Academic Publishers, pp.. 371–374.

Schweizer, P., Felix, G., Buchala, A., Muller, C. and Métraux, J.-P. (1996a) Perception of free cutin monomers by plant cells. Plant J. 10, 331–341.

Schweizer, P., Jeanguenat, A., Whitagre, D., Metraux, J.-P. and Mösinger, E. (1996b) Induction of resistance in barley against *Erysiphe graminis* f. sp. hordei by free cutin monomers. Physiol. Mol. Plant Pathol. 49, 103–120.

Shah, J., Tsui, F. and Klessig, D. F. (1997) Characterization of a salicylic acid-insensitive mutant (sail) of Arabidopsis thaliana, identified in a selective screen utilizing the SA-inducible expression of the tms2 gene. Mol. Plant-Microbe Interact. 10, 67–78.

Stapleton, A., Beetham, J. K., Pinot, F., Garbarino, J. E., Rockhold, D. R., Friedman, M., Hammock, B. and Belknap, W. R. (1994) Cloning and expression of soluble epoxide hydrolase from potato. Plant J. 6, 251–258.

Summermatter, K., Sticher, L. and Métraux, J. P. (1995) Systemic responses in Arabidopsis thaliana after infected and challenged with Pseudomonas syringae pv syringae. Plant Physiol. 108, 1379–1385.

Uknes, S., Winter, A. M., Delaney, T., Vernooij, B., Morse, A., Friedrich, L., Nye, G., Potter, S., Ward, E. and Ryals, J. (1993) Biological induction of systemic acquired resistance in Arabidopsis. Mol. Plant-Microbe Interact. 6, 692–698.

Van Rensburg, L. and Krüger, G. H. J. (1994) Evaluation of components of oxidative stress metabolism for use in selection of drought tolerant cultivars of Nicotiana tabacum L. J. Plant Physiol. 143, 730–737.

Vernooij, B., Friedrich, L., Ahl Goy, P., Staub, J., Kessmann, H. and Ryals, J. (1995) 2,6-Dichloroisonicotinic acid-induced resistance to pathogens without the accumulation of salicylic acid. Mol. Plant-Microbe Interact. 8, 228–234.

Vernooij, B., Friedrich, L., Morse, A., Reist, R., Kolditz-Jawhar, R., Ward, E., Uknes, S., Kessmann, H. and Ryals, J. (1994) Salicylic acid is not the translocated signal responsible for inducing systemic resistance but is required in signal transduction. Plant Cell 6, 959–965.

Vick, B. A. and Zimmerman, D. C. (1983) The biosynthesis of jasmonic acid: a physiological role for plant lipoxygenase. Biochem. Biophys. Res. Commun. 111, 470–477.

Vidal, S., de León, I. P., Denecke, J. and Palva, E. T. (1997) Salicylic acid and the plant pathogen *Erwinia carotovora* induce defense genes via antagonistic pathways. Plant J. 11, 115–123.

Ward, E. R., Uknes, S. J., Williams, S. C., Dincher, S. S., Wiederhold, D. L., Alexander, D. C., Ahl-Goy, P., Metraux, J. P. and Ryals, J. A. (1991) Coordinate gene activity in response to agents that induce systemic acquired resistance. Plant Cell 3, 1085–1094.

Wobbe, K. K. and Klessig, D. F. (1996) Salicylic acid—an important signal in plants. In Plant Gene Research (Dennis, E. S., Hohn, B., Hohn, Th., King, P. J., Schell, J. and Verma, D. P. S., eds.) Wein and New York: Springer-Verlag, pp. 167–196.

Xiang, C., Miao, Z-H. and Lam, E. (1996) Coordinated activation of as-1-type elements and a tobacco glutathione S-transferase gene by auxins, salicylic acid, methyl-jasmonate and hydrogen peroxide. Plant Mol. Biol. 32, 415–426.

Xu, Y., Chang, P. -F. L., Liu, D., Narasimhan, M. L., Raghothama, K. G., Hasegawa, P. M. and Bressan, R. A. (1994) Plant defense genes are synergistically induced by ethylene and methyl jasmonate. Plant Cell 6, 1077–1085.

Yalpani, N., Silverman, P., Wilson, T. M. A., Kleier, D. A. and Raskin, I. (1991) Salicylic acid is a systemic signal and an inducer of pathogenesis-related proteins in virus-infected tobacco. Plant Cell 3, 809–818.

Yang, Y., Shah, J. and Klessig, D. F. (1997) Signal perception and transduction in plant defense responses. Genes Dev. (in press).

Ziegler, J., Hamberg, M., Miersch, O. and Parthier, B. (1997) Purification and characterization of allene oxide cyclase from dry corn seeds. Plant Physiol. 114, 565–573.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for identifying compounds that activate a SI-SAR pathway in plants, comprising:
   a) providing a first DNA construct in which a first reporter gene is operably linked to a SIS gene promoter;
   b) providing a second DNA construct in which a second reporter gene is operably linked to a SA-inducible gene promoter;
   c) transforming a plant with the first and second DNA constructs;
   d) administering to the plant a test compound suspected of activating the SI-SAR pathway; and
   e) detecting expression of the first and second reporter genes, expression of the first reporter gene and lack of expression of the second reporter gene being indicative of activation of the SI-SAR pathway by the test compound.

2. A method for identifying compounds that activate a SI-SAR pathway in plants, comprising:
   a) providing a plant that does not accumulate endogenous SA;
   b) transforming the plant with a DNA construct comprising a reporter gene operably linked to a SIS gene promoter;
   c) administering to the plant a test compound suspected of activating the SI-SAR pathway; and
   d) detecting expression of the reporter gene, the expression of the reporter gene being indicative of activation of the SI-SAR pathway by the test compound.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 311 amino acids
      (B) TYPE: amino acid (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:1:

```
Met Glu Lys Ile Gln His Asn Tyr Val Asp Val Arg Gly Leu Lys Leu
 1               5                  10                  15

His Ile Ala Glu Ile Gly Thr Gly Pro Ala Val Phe Phe Leu His Gly
                20                  25                  30

Phe Pro Glu Ile Trp Tyr Ser Trp Arg His Gln Met Ile Ala Val Ala
            35                  40                  45

Asp Ala Gly Phe Arg Gly Ile Ala Pro Asp Phe Arg Gly Tyr Gly Leu
        50                  55                  60

Ser Glu Leu Pro Ala Glu Pro Glu Lys Thr Thr Phe Arg Asp Leu Val
65                  70                  75                  80

Asp Asp Leu Leu Asp Met Leu Asp Ser Leu Gly Ile His Gln Val Phe
                85                  90                  95

Leu Val Gly Lys Asp Phe Gly Ala Arg Val Ala Tyr His Phe Ala Leu
                100                 105                 110

Val His Pro Asp Arg Val Ser Thr Val Val Thr Leu Gly Val Pro Phe
            115                 120                 125

Leu Leu Thr Gly Pro Glu Thr Phe Pro Arg Asp Leu Ile Pro Asn Gly
        130                 135                 140

Phe Tyr Met Leu Arg Trp Gln Glu Pro Gly Arg Ala Glu Lys Asp Phe
145                 150                 155                 160

Gly Arg Phe Asp Thr Lys Thr Val Val Lys Asn Ile Tyr Thr Met Phe
                165                 170                 175

Ser Gly Ser Glu Leu Pro Ile Ala Lys Asp Asp Glu Glu Ile Met Asp
                180                 185                 190

Leu Val Asp Pro Ser Ala Pro Val Pro Asp Trp Phe Thr Gly Glu Asp
            195                 200                 205

Leu Ala Asn Tyr Ala Ser Leu Tyr Glu Lys Ser Ser Phe Arg Thr Ala
        210                 215                 220

Leu Gln Val Pro Tyr Arg Ala Trp Leu Glu Glu Tyr Gly Val Lys Asp
225                 230                 235                 240

Ile Lys Val Lys Val Pro Cys Leu Leu Val Met Gly Glu Lys Asp Tyr
                245                 250                 255

Ala Leu Lys Phe Gly Gly Leu Glu Gln Tyr Val Lys Ser Gly Met Val
                260                 265                 270

Lys Glu Tyr Val Pro Asn Leu Glu Thr Ile Phe Leu Pro Glu Gly Ser
            275                 280                 285

His Phe Val Gln Glu Gln Phe Pro Glu Gln Val Asn Gln Leu Ile Ile
        290                 295                 300

Thr Phe Leu Lys Lys Leu Ile
305                 310
```

(2) INFORMATION FOR SEQ ID NO:2:

(i) SEQUENCE CHARACTERISTICS:

(A) LENGTH: 1238 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

| | |
|---|---|
| AACACATTGA CTTGTCATTA ATTCTCTTTA ATTTTTGTTG CACTCCCATC AAACCTTCCT | 60 |
| ACCTTACGAA AATGGAGAAG ATTCAGCACA ATTATGTGGA TGTAAGAGGA CTCAAGCTTC | 120 |
| ACATTGCAGA GATTGGAACA GGCCCTGCAG TATTCTTTCT TCATGGATTC CCTGAGATAT | 180 |
| GGTACTCGTG GAGGCATCAG ATGATAGCAG TAGCGGATGC AGGATTTCGA GGCATAGCCC | 240 |
| CTGACTTCAG AGGCTATGGT TTGTCTGAAT TGCCTGCAGA ACCGGAGAAG ACGACATTCA | 300 |
| GGGACCTTGT CGATGATCTT CTGGACATGC TTGATTCATT AGGCATCCAC CAGGTTTTTC | 360 |
| TTGTGGGGAA GGATTTTGGA GCTCGAGTAG CTTACCATTT TGCACTCGTA CACCCTGATA | 420 |
| GAGTTTCAAC TGTTGTAACA TTAGGTGTGC CCTTTCTTCT CACTGGTCCA GAAACATTTC | 480 |
| CTCGAGATCT CATTCCCAAT GGGTTCTATA TGTTGAGATG GCAGGAACCA GGGCGAGCTG | 540 |
| AAAAGGACTT TGGGCGTTTT GATACAAAAA CAGTAGTTAA GAACATATAT ACTATGTTCT | 600 |
| CTGGAAGTGA ACTGCCAATT GCAAAAGATG ATGAGGAAAT AATGGATTTG GTTGATCCTT | 660 |
| CTGCTCCAGT GCCTGACTGG TTCACAGGAG AGGATCTTGC AAACTACGCA TCTCTTTACG | 720 |
| AAAAGTCAAG TTTCCGAACA GCATTGCAGG TGCCTTACAG GGCTTGGCTA GAAGAATATG | 780 |
| GAGTTAAAGA TATCAAAGTC AAGGTTCCCT GTTTGCTTGT AATGGGAGAG AAGGATTACG | 840 |
| CCCTAAATT TGGTGGATTA GAGCAATACG TTAAAAGTGG AATGGTGAAA GAATATGTGC | 900 |
| CTAATCTGGA AACCATATTC TTACCAGAAG GCAGTCATTT TGTACAAGAG CAGTTTCCTG | 960 |
| AACAGGTCAA TCAGTTGATT ATCACCTTCC TCAAAAAGCT CATATAATAA ACTGCTTGCC | 1020 |
| AGCGACGTTG AATAAAGGGC AACCCAGTGC ACGAAACTCC CGTTATGCAC AAGGTTTGGG | 1080 |
| AGGAGCCGGC ATTTGGGTCT TATTTTTCAG AGTTGAATGT TGATCTCAGT TTTATCAAAC | 1140 |
| AATACCATAT CACATTTTCG GCATATTTCT ACTTGTATGT TGATCAATAA AAGGGACGAT | 1200 |
| GGTTTACGCG CCTCAGTTCT AAAAAAAAAA AAAAAAA | 1238 |

(2) INFORMATION FOR SEQ ID NO:3:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
GTCCTACTCC ATATCTCATC TTCTTTTCTC TGTTAGCGCG GAGTTAGGGA CGCTAGGGGT    60

TCATCGTCAG AATCTTTTCG TCAGAAAATT ACACTCTATA TATATGCAG              109
```

(2) INFORMATION FOR SEQ ID NO:4:

(i) SEQUENCE CHARACTERISTICS:
        (A) LENGTH: 320 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:4:

```
Met Glu Lys Ile Glu His Lys Met Val Ala Val Asn Gly Leu Asn Met
 1               5                  10                  15

His Leu Ala Glu Leu Gly Glu Gly Pro Thr Ile Leu Phe Ile His Gly
                20                  25                  30

Phe Pro Glu Leu Trp Tyr Ser Trp Arg His Gln Met Tyr Leu Ala Glu
            35                  40                  45

Arg Gly Tyr Arg Ala Val Ala Pro Asp Leu Arg Gly Tyr Gly Asp Thr
        50                  55                  60

Thr Gly Ala Pro Leu Asn Asp Pro Ser Lys Phe Ser Ile Leu His Leu
65                  70                  75                  80

Val Gly Asp Val Val Ala Leu Leu Glu Ala Ile Ala Pro Asn Glu Glu
                85                  90                  95

Lys Val Phe Val Val Ala His Asp Trp Gly Ala Leu Ile Ala Trp His
                100                 105                 110

Leu Cys Leu Phe Arg Pro Asp Lys Val Lys Ala Leu Val Asn Leu Ser
            115                 120                 125

Val His Phe Ser Lys Arg Asn Pro Lys Met Asn Val Val Glu Gly Leu
        130                 135                 140

Lys Ala Ile Tyr Gly Glu Asp His Tyr Ile Ser Arg Phe Gln Val Pro
145                 150                 155                 160

Gly Glu Ile Glu Ala Glu Phe Ala Pro Ile Gly Ala Lys Ser Val Leu
                165                 170                 175

Lys Lys Ile Leu Thr Tyr Arg Asp Pro Ala Pro Phe Tyr Phe Pro Lys
            180                 185                 190

Gly Lys Gly Leu Glu Ala Ile Pro Asp Ala Pro Val Ala Leu Ser Ser
        195                 200                 205

Trp Leu Ser Glu Glu Glu Leu Asp Tyr Tyr Ala Asn Lys Phe Glu Gln
210                 215                 220

Thr Gly Phe Thr Gly Ala Val Asn Tyr Tyr Arg Ala Leu Pro Ile Asn
225                 230                 235                 240

Trp Glu Leu Thr Ala Pro Trp Thr Gly Ala Gln Val Lys Val Pro Thr
                245                 250                 255

Lys Phe Ile Val Gly Glu Phe Asp Leu Val Tyr His Ile Pro Gly Ala
            260                 265                 270

Lys Glu Tyr Ile His Asn Gly Gly Phe Lys Lys Asp Val Pro Leu Leu
        275                 280                 285
```

-continued

```
Glu Glu Val Val Val Leu Glu Gly Ala Ala His Phe Val Ser Gln Glu
    290                 295                 300
Arg Pro His Glu Ile Ser Lys His Ile Tyr Asp Phe Ile Gln Lys Phe
305                 310                 315                 320
```

(2) INFORMATION FOR SEQ ID NO:5:

(i) SEQUENCE CHARACTERISTICS:
        (A) LENGTH: 321 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:5:

```
Met Glu His Arg Lys Val Arg Gly Asn Gly Ile Asp Ile His Val Ala
1               5                   10                  15
Ile Gln Gly Pro Ser Asp Gly Pro Ile Val Leu Leu His Gly Phe
                20                  25                  30
Pro Glu Leu Trp Tyr Ser Trp Arg His Gln Ile Pro Gly Leu Ala Ala
            35                  40                  45
Arg Gly Tyr Arg Ala Val Ala Pro Asp Leu Arg Gly Tyr Gly Asp Ser
50                  55                  60
Asp Ala Pro Ala Glu Ile Ser Ser Tyr Thr Cys Phe Asn Ile Val Gly
65                  70                  75                  80
Asp Leu Ile Ala Val Ile Ser Ala Leu Thr Ala Ser Glu Asp Glu Lys
                85                  90                  95
Val Phe Val Gly His Asp Trp Gly Ala Leu Ile Ala Trp Tyr Leu
                100                 105                 110
Cys Leu Phe Arg Pro Asp Arg Val Lys Ala Leu Val Asn Leu Ser Val
            115                 120                 125
Pro Phe Ser Phe Arg Pro Thr Asp Pro Ser Val Lys Pro Val Asp Arg
130                 135                 140
Met Arg Ala Phe Tyr Gly Asp Asp Tyr Tyr Ile Cys Arg Phe Gln Glu
145                 150                 155                 160
Phe Gly Asp Val Glu Ala Glu Ile Ala Glu Val Gly Thr Glu Arg Val
                165                 170                 175
Met Lys Arg Leu Leu Thr Tyr Arg Thr Pro Gly Pro Val Ile Ile Pro
            180                 185                 190
Lys Asp Lys Ser Phe Trp Gly Ser Lys Gly Glu Thr Ile Pro Leu Pro
            195                 200                 205
Ser Trp Leu Thr Glu Glu Asp Val Ala Tyr Phe Val Ser Lys Phe Glu
            210                 215                 220
Glu Lys Gly Phe Ser Gly Pro Val Asn Tyr Tyr Arg Asn Phe Asn Arg
225                 230                 235                 240
Asn Asn Glu Leu Leu Gly Pro Trp Val Gly Ser Lys Ile Gln Val Pro
                245                 250                 255
Thr Lys Phe Val Ile Gly Glu Leu Asp Leu Val Tyr Tyr Met Pro Gly
            260                 265                 270
```

-continued

Val Lys Glu Tyr Ile His Gly Pro Gln Phe Lys Glu Asp Val Pro Leu
          275                 280                 285

Leu Glu Glu Pro Val Val Met Glu Gly Val Ala His Phe Ile Asn Gln
          290                 295                 300

Glu Lys Pro Gln Glu Ile Leu Gln Ile Ile Leu Asp Phe Ile Ser Lys
305                 310                 315                 320

Phe (2) INFORMATION FOR SEQ ID NO:6:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:6:

Met Ala Leu Arg Val Ala Ala Phe Asp Leu Asp Gly Val Leu Ala Leu
1                 5                   10                  15

Pro Ser Ile Ala Gly Val Leu Arg His Thr Glu Glu Ala Leu Ala Leu
              20                  25                  30

Pro Arg Asp Phe Leu Leu Gly Ala Phe Gln Met Lys Phe Pro Glu Gly
              35                  40                  45

Pro Thr Glu Gln Leu Met Lys Gly Lys Ile Thr Phe Ser Gln Trp Val
50                  55                  60

Pro Leu Met Asp Glu Ser Cys Arg Lys Ser Ser Lys Ala Cys Gly Ala
65                  70                  75                  80

Ser Leu Pro Glu Asn Phe Ser Ile Ser Glu Ile Phe Ser Gln Ala Met
              85                  90                  95

Ala Ala Arg Ser Ile Asn Arg Pro Met Leu Gln Ala Ala Ala Ala Leu
              100                 105                 110

Lys Lys Lys Gly Phe Thr Thr Cys Ile Val Thr Asn Asn Trp Leu Asp
              115                 120                 125

Asp Ser Asp Lys Arg Asp Ile Leu Ala Gln Met Met Cys Glu Leu Ser
130                 135                 140

Gln His Phe Asp Phe Leu Ile Glu Ser Cys Gln Val Gly Met Ile Lys
145                 150                 155                 160

Pro Glu Pro Gln Ile Tyr Lys Phe Val Leu Asp Thr Leu Lys Ala Lys
              165                 170                 175

Pro Asn Glu Val Val Phe Leu Asp Asp Phe Gly Ser Asn Leu Lys Pro
              180                 185                 190

Ala Arg Asp Met Gly Met Val Thr Ile Leu Val Arg Asp Thr Ala Ser
              195                 200                 205

Ala Leu Arg Glu Leu Glu Lys Val Thr Gly Thr Gln Phe Pro Glu Ala
              210                 215                 220

Pro Leu Pro Val Pro Cys Ser Pro Asn Asp Val Ser His Gly Tyr Val
225                 230                 235                 240

Thr Val Lys Pro Gly Ile Arg Leu His Phe Val Glu Met Gly Ser Gly
              245                 250                 255

```
Pro Ala Ile Cys Leu Cys His Gly Phe Pro Glu Ser Trp Phe Ser Trp
            260                 265                 270

Arg Tyr Gln Ile Pro Ala Leu Ala Gln Ala Gly Phe Arg Val Leu Ala
        275                 280                 285

Ile Asp Met Lys Gly Tyr Gly Asp Ser Ser Pro Glu Ile Glu
290                 295                 300

Glu Tyr Ala Met Glu Leu Leu Cys Glu Glu Met Val Thr Phe Leu Asn
305                 310                 315                 320

Lys Leu Gly Ile Pro Gln Ala Val Phe Ile Gly His Asp Trp Ala Gly
                325                 330                 335

Val Leu Val Trp Asn Met Ala Leu Phe His Pro Glu Arg Val Arg Ala
            340                 345                 350

Val Ala Ser Leu Asn Thr Pro Leu Met Pro Pro Asn Pro Glu Val Ser
            355                 360                 365

Pro Met Glu Val Ile Arg Ser Ile Pro Val Phe Asn Tyr Gln Leu Tyr
            370                 375                 380

Phe Gln Glu Pro Gly Val Ala Glu Ala Glu Leu Glu Lys Asn Met Ser
385                 390                 395                 400

Arg Thr Phe Lys Ser Phe Phe Arg Thr Ser Asp Asp Met Gly Leu Leu
                405                 410                 415

Thr Val Asn Lys Ala Thr Glu Met Gly Gly Ile Leu Val Gly Thr Pro
                420                 425                 430

Glu Asp Pro Lys Val Ser Lys Ile Thr Thr Glu Glu Ile Glu Tyr
            435                 440                 445

Tyr Ile Gln Gln Phe Lys Lys Ser Gly Phe Arg Gly Pro Leu Asn Trp
450                 455                 460

Tyr Arg Asn Thr Glu Arg Asn Trp Lys Trp Ser Cys Lys Ala Leu Gly
465                 470                 475                 480

Arg Lys Ile Leu Val Pro Ala Leu Met Val Thr Ala Glu Lys Asp Ile
                485                 490                 495

Val Leu Arg Pro Glu Met Ser Lys Asn Met Glu Asn Trp Ile Pro Phe
            500                 505                 510

Leu Lys Arg Gly His Ile Glu Asp Cys Gly His Trp Thr Gln Ile Glu
            515                 520                 525

Lys Pro Ala Glu Val Asn Gln Ile Leu Ile Lys Trp Leu Lys Thr Glu
            530                 535                 540

Ile Gln Asn Pro Ser Val Thr Ser Lys Ile
545                 550

(2) INFORMATION FOR SEQ ID NO:7:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:7:
```

-continued

```
Met Thr Leu Arg Gly Ala Val Phe Asp Leu Asp Gly Val Leu Ala Leu
 1               5                  10                  15

Pro Ala Val Phe Gly Val Leu Gly Arg Thr Glu Glu Ala Leu Ala Leu
             20                  25                  30

Pro Arg Gly Leu Leu Asn Asp Ala Phe Gln Lys Gly Gly Pro Glu Gly
         35                  40                  45

Ala Thr Thr Arg Leu Met Lys Gly Glu Ile Thr Leu Ser Gln Trp Ile
     50                  55                  60

Pro Leu Met Glu Glu Asn Cys Arg Lys Cys Ser Glu Thr Ala Lys Val
 65                  70                  75                  80

Cys Leu Pro Lys Asn Phe Ser Ile Lys Glu Ile Phe Asp Lys Ala Ile
                 85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
            115                 120                 125

Asp Arg Ala Glu Arg Asp Gly Leu Ala Gln Leu Met Cys Glu Leu Lys
        130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365

Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
```

-continued

```
                    420                    425                    430
Glu Glu Pro Ser Leu Ser Arg Met Val Thr Glu Glu Glu Ile Gln Phe
        435                    440                    445

Tyr Val Gln Gln Phe Lys Lys Ser Gly Phe Arg Gly Pro Leu Asn Trp
    450                    455                    460

Tyr Arg Asn Met Glu Arg Asn Trp Lys Trp Ala Cys Lys Ser Leu Gly
465                    470                    475                    480

Arg Lys Ile Leu Ile Pro Ala Leu Met Val Thr Ala Glu Lys Asp Phe
                485                    490                    495

Val Leu Val Pro Gln Met Ser Gln His Met Glu Asp Trp Ile Pro His
            500                    505                    510

Leu Lys Arg Gly His Ile Glu Asp Cys Gly His Trp Thr Gln Met Asp
        515                    520                    525

Lys Pro Thr Glu Val Asn Gln Ile Leu Ile Lys Trp Leu Asp Ser Asp
    530                    535                    540

Ala Arg Asn Pro Pro Val Val Ser Lys Met
545                    550
```